United States Patent [19]
Arnold

[11] 3,972,706
[45] Aug. 3, 1976

[54] HERBICIDAL METHOD

[75] Inventor: Wendell Ray Arnold, Delray Beach, Fla.

[73] Assignee: Eli Lilly and Company, Indianapolis, Ind.

[22] Filed: Dec. 18, 1974

[21] Appl. No.: 533,897

Related U.S. Application Data

[63] Continuation of Ser. No. 374,598, June 28, 1973, abandoned.

[52] U.S. Cl.......................................... 71/90; 71/88
[51] Int. Cl.².......................................... A01N 9/12
[58] Field of Search ................................. 71/90

[56] References Cited
UNITED STATES PATENTS

| | | | |
|---|---|---|---|
| 3,565,901 | 2/1971 | Cebalo | 71/90 |
| 3,726,892 | 4/1973 | Cebalo | 71/90 |

FOREIGN PATENTS OR APPLICATIONS

| | | | |
|---|---|---|---|
| 765,930 | 9/1971 | Belgium | 71/90 |

OTHER PUBLICATIONS

Wicks, et al., "Chemical Fallow in a Winter, etc.;" (1972) Weed Science 21 pp. 97–102 (1973).

*Primary Examiner*—Glennon H. Hollrah
*Attorney, Agent, or Firm*—Dwight E. Morrison; Everet F. Smith

[57] ABSTRACT

There is disclosed a method of controlling unwanted vegetation in fallow wheatland by the application of a substituted thiadiazol-2-ylurea following the harvesting of the wheat crop.

4 Claims, No Drawings

HERBICIDAL METHOD

This is a continuation of application Ser. No. 374,598, filed June 28, 1973, now abandoned.

BACKGROUND OF THE INVENTION

1. Field of the Invention

The control of weeds which grow in a wheat field after the wheat crop has been harvested has long been a problem to wheat farmers. The growth of the weeds has several disadvantages. The weeds, by their presence and growth, take needed moisture and nutrients from the soil, and prevention of this loss of moisture is particularly important in winter wheat production because of the relative scarcity of rainfall in those regions where winter wheat is grown. Further, the weeds are of no use as fodder for the farm animals. When the weeds mature, the seeds which are produced at maturity are scattered by the winds, birds, and animals, so that the infestation of weeds spreads far beyond the confines of the particular field.

2. Description of the Prior Art

The usual method of controlling the weeds in fallow wheatland has been to plow the field periodically, or otherwise cultivate it to kill the weeds. These operations kill the weeds so they do not mature and produce additional seeds, and so that the depletion of water from the soil by the weeds is prevented. The plowing and other cultivations do make the soil more friable and more receptive to rainfall, and the rainwater thereby does not run off and become lost.

However, the disadvantages of the usual method of controlling weeds in fallow wheatland are of such significance they are not to be overlooked. Control of the weeds by plowing usually requires about five plowings between the time of harvesting the wheat 1 year and the seeding of the new crop approximately 1 year later. Such plowings take time to accomplish. There is additional wear and tear on the machineary used by the wheat producer to accomplish the cultivations. The additional cultivations also loosen the soil and thus permit greater wind erosion of the soil. In addition, there is the increased consumption of fuel to power the machinery used in the cultivations. There would thus be significant overall savings to the producer together with benefit to the ecology if the number of man and machine operations on the soil could be reduced.

While the prior art refers to many thiadiazoles and derivatives thereof, none of the prior art is believed to be an enabling disclosure of the specific use disclosed herein. Some related compounds shown in the prior art, such as, for example, 1-(5-methyl-1,3,4-thiadiazol-2-yl)-3-phenylthiourea and 1-(5-methyl-1,3,4-thiadiazol-2-yl)-3-phenylurea [J. Pharm. Soc., Japan 74, 1044–1048 (1954); C.A. 49, 11630 (1955)] were not reported to have biological activity.

An article in Farmaco Ed. Sci. 22 (6), 393-401 (1967), discloses the use of 1-(5-alkyl-1,3,4-thiadiazol-2-yl)ureas as intermediates for the production of isomeric 1,3-bis-(5-alkyl-1,3,4-thiadiazol-2-yl) ureas, which latter compounds are alleged to exhibit hypoglycemic action. These compounds are only generally related to those used in the practice of the instant invention.

In U.S. Pat. No. 3,565,901 (Feb. 23, 1971), are taught salts of certain thiadiazol-2-ylureas alleged to be useful in agriculture applications as phytotoxicants. These salts are formed by thiadiazol-2-ylureas unsubstituted on the urea nitrogen closest to the thiadiazole ring. There is no mention of possible utility of the compounds in the cultivation of winter wheat and no test data regarding safety to winter wheat.

Belgian Pat. No. 765,930, teaches the use of 1,3-dimethyl-1-(5-tert.-butyl-1,3,4-thiadiazol-2-yl)urea, and 1-ethyl-1-(5-tert.-butyl-1,3,4-thiadiazol-2-yl)-3-methylurea, as pre- and postemergence herbicides on plant crops such as corn, cotton, peanuts, sorghum, and sugarcane. Data in this Belgian patent show that corn, cotton, sorghum, and wheat are largely destroyed by either pre- or postemergence application of from about 1 to about 5 pounds per acre of 1,3-dimethyl-3-(5-t-butyl-1,3,4-thiadiazol-2-yl)urea. This compound can also be named 1-(5-t-butyl-1,3,4-thiadiazol-2-yl)-1,3-dimethylurea, and is one of the compounds disclosed in the instant application as being useful in the instant novel method. According to the Belgian patent, preemergence application of the same compound at rates of about 1 to about 10 pounds per acre to corn and cotton resulted in "no effect" to "destroyed." The Belgian patent also reports that the same treatments using 1-ethyl-1-(5-t-butyl-1,3,4-thiadiazol-2-yl)-3-methylurea on corn, cotton, and sorghum, produced results ranging from "little effect" to "destroyed." The Belgian patent makes no suggestion that the compounds would be useful in the control of unwanted vegetation by preemergent application to a field wherein winter wheat is to be subsequently planted and grown.

In addition, Belgian Pat. No. 744,812, teached substituted 1,3,4-thiadiazoles, and alleges their utility as preemergence and/or postemergence herbicides, and as defoliants and dessicants of plants. No teaching of utility as selective herbicides appear to be present.

British Pat. No. 1,195,672, published June 17, 1970, teaches thiadiazoles alleged to possess utility as pre- and/or postemergence herbicides, together with herbicidal compositions containing the thiadiazoles as active ingredient, and a method of controlling plant growth. No suggestion that any of the compounds would be suitably selective for use as herbicides in the cultivation of winter wheat is present and winter wheat is not mentioned in the patent.

Yet another British Pat. No. 1,230,432, published May 5, 1971, is concerned with N-substituted 5-amino-1,3,4-thiadiazoles, the processes for their production, and their use as herbicides. A number of plants, including cotton, carrots, coffee, beans, beets, sugarcane, potatoes, bluegrass, barley, and wheat, as well as mustard, common chickweed, fescue, foxtail, and the like, are listed as susceptible to control by the N-substituted thiadiazoles. Thus, the control of desirable crop plants is made synonymous with the control of weed plants.

Still another British Pat. No. 1,254,468, published Nov. 24, 1971, is directed to 5-substituted 1,3,4-thiadiazolylureas, to processes for the production thereof, and to herbicidal compositions containing the named compounds. Utility for the control of weeds and wild grasses is alleged. No teaching is present of possible selectivity of herbicidal action of the compounds, nor utility in the cultivation of winter wheat.

British Pat. No. 1,266,172, published Mar. 8, 1972, is directed to substituted thiadiazole compounds and alleges their utility as herbicides, fungicides, acaricides, or insecticides. There appears to be no allegation in the British patent that the compounds listed therein would be useful as selective herbicides in the cultivation of winter wheat.

Kubo et al., J. Agr. Food Chem. 18 (1) 60–65 (1970), teach the results of the study of the preemergence and postemergence herbicidal activity of a number of 1-substituted-3-(5-substituted-1,3,4-thiadiazol-2-yl)ureas. The compound, 1-methyl-3-(5-t-butyl-1,3,4-thiadiazol-2-yl)urea, is reported as a strikingly phytotoxic compound. These authors report that this compound completely killed wheat when applied at the rate of 4.45 pounds per acre postemergence, but that it caused only slight damage to the wheat when applied at the same rate preemergence the day the seed was planted. However, preemergence tests in our laboratories using this compound at rates of 1, 2, and 4 pounds per acre killed the wheat.

Also in the prior art is British Pat. No. 1,297,147, published Nov. 22, 1972, which teaches 1,3,4-thiadiazolyl-(5)-ureas and their use as pre- or postemergence herbicides. The compounds are alleged to be particularly well suited for selective weed control in cereals, cotton, and carrots. In general, the application rate is taught as being from 0.9 to 110 lbs./acre, preferably from 1.9 to 44 lbs./acre. There is no teaching or disclosure suggesting use on fallow wheatland in the cultivation of winter wheat. In general, with few exceptions, the compounds tested killed wheat plants when applied either pre- or postemergent, according to the data disclosed in the patent.

A number of 2-ureido-5-sulphonamidothiazoles, alleged to possess utility as herbicides, are disclosed by West German Pat. No. 2,050,979, by Netherlands Pat. No. 7,015,249, and by Belgian Pat. No. 757,655. The abstracts of these publications, as appearing in Derwent, do not appear to suggest that the compounds were intended for use for the control of weeds in fallow wheatland.

The search continues for a satisfactory method of controlling the growth of unwanted vegetation in fallow winter wheatland, which method reduces the need to cultivate the land numerous times.

SUMMARY OF THE INVENTION

It is an object of this invention to provide methods for controlling unwanted vegetation in fallow wheatland.

In fulfillment of this object, this invention provides a novel method which comprises applying to a field from which the wheat has been harvested, an herbicidally-effective amount of one or more thiadiazole derivatives having the formula:

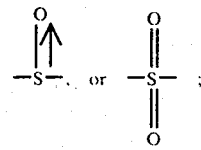
(I)

wherein
R is R$^1$X—,

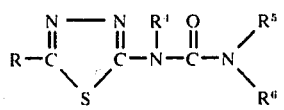

alkyl, or halogenated alkyl, each halogen being independently selected from the group consisting of fluorine, chlorine, and bromine;
R$^1$ is lower alkyl or C$_3$-C$_7$ cycloalkyl;
X is —S—,

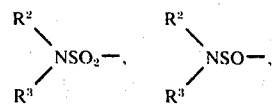

R$^2$ is hydrogen or a substituted or unsubstituted lower alkyl, the substituents being selected from the class consisting of halo, hydroxy, cyano, and lower alkoxy;
R$^3$ is lower alkoxy or a substituted or unsubstituted lower alkyl, the substituents being selected from the class consisting of halo, hydroxy, cyano, and lower alkoxy;
R$^2$ and R$^3$, when taken together with the nitrogen to which they are attached, form a morpholino, piperidino, or pyrrolidino group;
R$^4$ is hydrogen or lower alkyl;
R$^5$ is hydrogen, lower alkyl, lower alkenyl, or C$_3$-C$_7$ cycloalkyl; and
R$^6$ is hydrogen, lower alkenyl, C$_3$-C$_7$ cycloalkyl, lower alkoxy, or a substituted or unsubstituted lower alkyl, the substituents being selected from the group consisting of halo, hydroxy, cyano, or lower alkoxy, except that R$^5$ and R$^6$ cannot both be hydrogen or a C$_3$-C$_7$ cycloalkyl; and
tautomers of (I) wherein R$^4$ is hydrogen; and
when R$^4$ is hydrogen, the alkaline earth metal, alkali metal, and ammonium salts thereof.

DETAILED DESCRIPTION OF THE INVENTION

This invention relates to novel methods of the control of unwanted vegetation. More particularly, this invention relates to novel herbicidal methods for the control of unwanted vegetation in fallow wheatland, in which herbicidal methods the herbicidal compound has the formula:

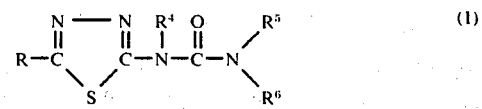
(I)

wherein
R is R$^1$X,

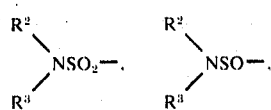

alkyl, or halogenated alkyl, each halogen being independently selected from the group consisting of fluorine, chlorine, and bromine;
R$^1$ is lower alkyl or C$_3$-C$_7$ cycloalkyl;
X is —S—,

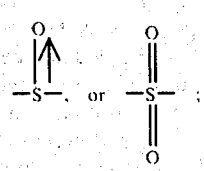

R² is hydrogen or a substituted or unsubstituted lower alkyl, the substituents being selected from the class consisting of halo, hydroxy, cyano, and lower alkoxy;

R³ is lower alkoxy or a substituted or unsubstituted lower alkyl, the substituents being selected from the class consisting of halo, hydroxy, cyano, and lower alkoxy;

R² and R³, when taken together with the nitrogen to which they are attached, form a morpholino, piperidino, or pyrrolidino group;

R⁴ is hydrogen or lower alkyl;

R⁵ is hydrogen, lower alkyl, lower alkenyl, or $C_3$-$C_7$ cycloalkyl; and

R⁶ is hydrogen, lower alkenyl, $C_3$-$C_7$ cycloalkyl, lower alkoxy, or a substituted or unsubstituted lower alkyl, the substituents being selected from the group consisting of halo, hydroxy, cyano, or lower alkoxy, except that R⁵ and R⁶ cannot both be hydrogen or a $C_3$-$C_7$ cycloalkyl; and, tautomers of (I) wherein R⁴ is hydrogen; and when R⁴ is hydrogen, the alkali metal, alkaline earth metal and ammonium salts thereof.

In the above formula, alkyl and lower alkyl mean straight or branched chain $C_1$-$C_7$ alkyl, such as methyl, ethyl, n-propyl, isopropyl, n-butyl, sec.-butyl, t-butyl, n-pentyl, 2-pentyl, 3-pentyl, 2-methyl-2-butyl, n-hexyl, 2-hexyl, 3-hexyl, 1,1-dimethylpropyl, 3-methyl-3-pentyl, n-heptyl, 2-heptyl, 3-heptyl, 4-heptyl, 1,1-dimethylbutyl, and the like.

In the above formula (I), when R is alkyl, it is preferably an alkyl branched at the α-carbon atom, that is, an alkyl group containing a side chain on the carbon atom that is attached to the thiadiazole nucleus; e.g., isopropyl, t-butyl, 2-butyl, 2-pentyl, 2-hexyl, 2-heptyl, 1-ethylpentyl, 1,1-dimethylpropyl, and the like.

Lower alkenyl means $C_2$-$C_7$ alkenyl, illustratively vinyl, allyl, 1-propenyl, crotyl, methallyl, 3-pentenyl, 5-hexenyl, 1-methyl-3-hexenyl, and the like.

Halogenated derivative of alkyl include $CF_3-$, $CF_3CF_2-$, $BrCH_2CH_2-$, $ClF_2C-$, $ClCH_2CH_2-$, $CF_3CF_2CF_2-$, $HCF_2CF_2-$, $(ClCH_2)_3C-$, $(ClCH_2)_2(CH_3)C-$, $(ClCH_2)(CH_3)_2C-$, and the like.

$C_3$-$C_7$ cycloalkyl refers to saturated cycloalkyl, and means cyclopropyl, cyclobutyl, cyclopentyl, cyclohexyl, and cycloheptyl, respectively.

Lower alkoxy means $C_1$-$C_4$ alkoxy and includes methoxy, ethoxy, n-propoxy, isopropoxy, n-butoxy, isobutoxy, sec.- butoxy, or t-butoxy.

Halo means bromo, chloro, and fluoro.

Metal refers to alkali and alkaline earth metals such as sodium, potassium, lithium, strontium, calcium, barium, magnesium, and includes any monovalent or polyvalent metal which will form a thiadiazolylurea derivative having salt-like or chelate characteristics.

Ammonium refers to ammonia.

Compounds coming within the scope of the generic formula (I), supra, include, but are not limited to the following:

1,3-Dimethyl-3-(5-trifluoromethyl-1,3,4-thiadiazol-2-yl)urea
1,3-Dimethyl-3-(5-t-butyl-1,3,4-thiadiazol-2-yl)urea
1,3-Dimethyl-3-(5-methylthio-1,3,4-thiadiazol-2-yl)urea
1,3-Dimethyl-3-(5-methylsulfonyl-1,3,4-thiadiazol-2-yl)urea
1,3-Dimethyl-3-(5-butylthio-1,3,4-thiadiazol-2-yl)urea
1,3-Dimethyl-3-(5-butylsulfonyl-1,3,4-thiadiazol-2-yl)urea
1-Methyl-1-methoxy-3-(5-methylthio-1,3,4-thiadiazol-2-yl)urea
1-Methyl-1-methoxy-3-(5-methylsulfonyl-1,3,4-thiadiazol-2-yl)urea
1-Butyl-1-methyl-3-(5-methylthio-1,3,4-thiadiazol-2-yl)urea
1-Butyl-1methyl-3-(5-methylsulfonyl-1,3,4-thiadiazol-2-yl)urea
1-Methyl-3-(5-pentafluoroethyl-1,3,4-thiadiazol-2-yl)urea
1-Methyl-3-[5-(β-chloroethyl)-1,3,4-thiadiazol-2-yl]urea
1,1,3-Trimethyl-3-(5-t-butyl-1,3,4-thiadiazol-2-yl)urea
1,1-Dimethyl-3-ethyl-3-[5-(dimethylsulfamoyl)-1,3,4-thiadiazol-2-yl]urea
1,3-Dimethyl-3-[5-(methylsulfamoyl)-1,3,4-thiadiazol-2-yl]urea
1,3-Dimethyl-3-[5-(2-chloro-1,1-dimethyl)ethyl-1,3,4-thiadiazol-2-yl]urea
1-Methoxy-1-methyl-3-(5-t-butyl-1,3,4-thiadiazol-2-yl)urea
1,3-Dimethyl-3-[5-(dimethylsulfamoyl)-1,3,4-thiadiazol-2-yl]urea
1,1,3-Trimethyl-3-[5-(dimethylsulfamoyl)-1,3,4-thiadiazol-2-yl]urea
1,1-Dimethyl-3-ethyl-3-[5-(dimethylaminosulfinyl)-1,3,4-thiadiazol-2-yl]urea
1,3-Dimethyl-3-[5-(methylaminosulfinyl)-1,3,4-thiadiazol-2-yl]urea
1,1,3-Trimethyl-3-[5-(dimethylaminosulfinyl)-1,3,4-thiadiazol-2-yl]urea
1-Methyl-3-[5-(β-bromoethyl)-1,3,4-thiadiazol-2-yl]urea
1-Methyl-3-(5-chlorodifluoromethyl-1,3,4-thiadiazol-2-yl)urea
1,3-Dimethyl-3-(5-heptafluoropropyl-1,3,4-thiadiazol-2-yl)urea
1-Butyl-1-methyl-3-(5-dimethylsulfamoyl-1,3,4-thiadiazol-2-yl)urea
1-Cyclopropyl-3-(5-dimethylsulfamoyl-1,3,4-thiadiazol-2-yl)urea
1-Methyl-3-(5-morpholinosulfonyl-1,3,4-thiadiazol-2-yl)urea
1,3-Dimethyl-3-(5-dimethylsulfamoyl-1,3,4-thiadiazol-2-yl)urea
1-Methyl-1-methoxy-3-(5-dimethylsulfamoyl-1,3,4-thiadiazol-2-yl)urea
1-Methyl-3-(5-N-butyl-N-methylsulfamoyl-1,3,4-thiadiazol-2-yl)urea
1-Methyl-3-(5-N-butylsulfamoyl-1,3,4-thiadiazol-2-yl)urea
1-Methyl-3-(5-N,N-dipropylsulfamoyl-1,3,4-thiadiazol-2-yl)urea
1-Methyl-3-(5-N-allylsulfamoyl-1,3,4-thiadiazol-2-yl)urea, and the like.

It has been found that when a thiadiazol-2-ylurea coming within the scope of the above structural formula (I) is applied to the soil at a rate of from about 0.5 to about 2 pounds per acre, preferably at a rate of from about 0.5 to about 1.0 pound per acre, after the wheat has been harvested, almost complete control is obtained of the undesirable weeds and grasses which usually grow on fallow wheatland between the time of the wheat harvest in 1 year and the time of planting the winter wheat approximately a year later.

This control is accomplished without the necessity of the five or more plowings or cultivations usually required to destroy the unwanted vegetation and to prevent the loss of moisture from the soil caused by the growth of the unwanted vegetation. Thus, the number of plowings or cultivations of the field is reduced to about two, producing a large saving in time and effort for the wheat grower. The reduction in the number of cultivations also decreases the chances of wind erosion of the loosened soil. The amount of fuel needed to power the machinery is decreased, as well as the wear and tear on the machinery.

In one embodiment of the invention, the thiadiazol-2-ylurea is surface applied to the field of wheat stubble within a few days or within a few weeks of the harvesting of the wheat. The field then remains undisturbed and lies fallow over the winter, during which time the herbicidal effect of the thiadiazol-2-ylurea is utilized. About July, in the year following the application of the herbicide, the stubble ground is plowed, disced, or undercut. The tillage of the stubble ground is the first step in the process of preparing the soil to receive summer rains and for seeding to winter wheat in the fall.

In a second embodiment of the invention, the thiadiazol-2-ylurea is applied about 8 or 9 months after the harvest of the wheat, that is, in about March or April in the spring of the year following the wheat harvest. In this embodiment, the wheat stubble may be undercut soon after the harvest, and the herbicide applied about 8 or 9 months later.

In either embodiment, the winter wheat is then planted at the normal and usually scheduled time, which is approximately 1 year after the previous harvest. Prior to planting, the field is prepared to receive the wheat seed.

The usual and customary procedure for preparing the land for planting of the winter wheat understandably varies in different portions of the country, due both to the type of soil and to the farming customs of the various areas of the country. For example, in western Kansas, the wheat producer prepares the soil by plowing and then tilling with a rod weeder, following which preparation the wheat is planted. In western Nebraska, the customary method is to turn the soil over with a one-way implement, that is, a single set of discs. Following this treatment of the soil, the wheat is planted by drilling in the customary manner.

The weeds which it has been found possible to control by this novel method include, but are not limited to the following: witchgrass (*Panicum capillare*), Russian thistle (*Salsola kalit*), Kochia or Mexican fireweed (*Kochia scoparia*), pigweed (*Amaranthus sp.*), as well as stink grass or love grass (*Eragrostis cilianensis*), downy bromegrass (*Bromus tectorum*), wild mustard (*Brassica kaber*), sunflower (*Helianthus annuus*), lambsquarter (*Chenopodium album*), and volunteer wheat (*Triticum sp.*).

The compounds useful in the novel herbicidal process of this invention may be prepared by methods which are normally employed for the synthesis of urea derivatives and which are well documented in the chemical literature. For example, ureas may be prepared by the reaction of an amine with an isocyanate to give the corresponding urea. See reaction a), below. A catalyst can be employed in this reaction as, for example, triethylamine, dibutyltin, diacetate, 1,4-diazabicyclo(2.2.2)octane and the like.

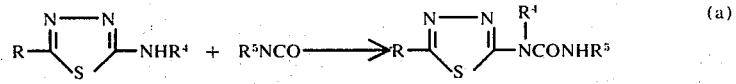

Another reaction employed to give the desired end product is that in which the amine is reacted with phosgene to give an intermediate carbamoyl chloride. An acid-fixing agent, e.g. triethylamine, or a catalyst such as boron trifluoride-ether complex may be employed in this reaction. The final product is obtained by reacting the intermediate with a primary or secondary amine, as shown by reaction (b), below.

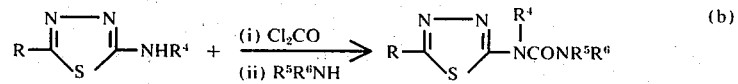

Another useful method for obtaining urea products is that in which a primary amine is reacted with N,N'-carbonyldiimidazole to give an intermediate imidazolylurea. The resulting urea is then further reacted with a primary or secondary amine to give the desired urea product, as outlined below in reaction (c).

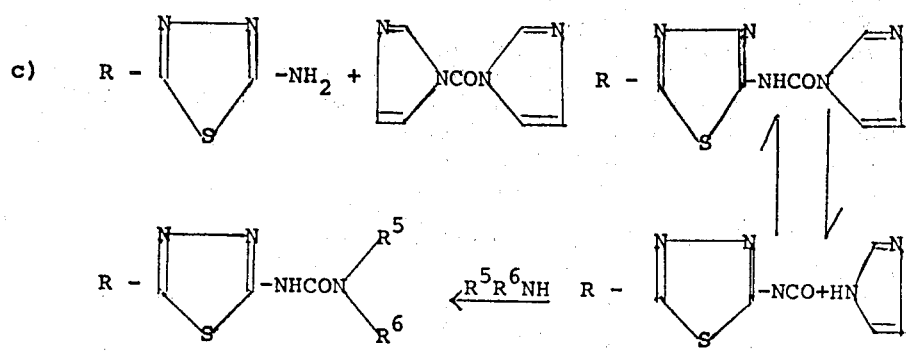

A further method employed is that in which metal derivatives of an amine are reacted with either an N,N-disubstituted carbamoyl chloride to give the desired end product or with phosgene to give an intermediate carbamoyl chloride which is then reacted with an amine to also give the desired end product. Such metal derivatives of the amine reactant may be sodium, potassium, or lithium. The following general reactions (d) and (e), are illustrative of the above.

X=Na, K or Li
R, $R^4$, $R^5$ and $R^6$ are as described previously.

For given substituents, R and $R^4$, each of the above methods will give a different yield. Selection of the preferred method, consequently, is an empirical decision based on experience with given substituents.

Additionally, those compounds having an alkylsulfonyl substituent in the 5-position of the thiadiazole, and useful in the novel herbicidal process of this invention

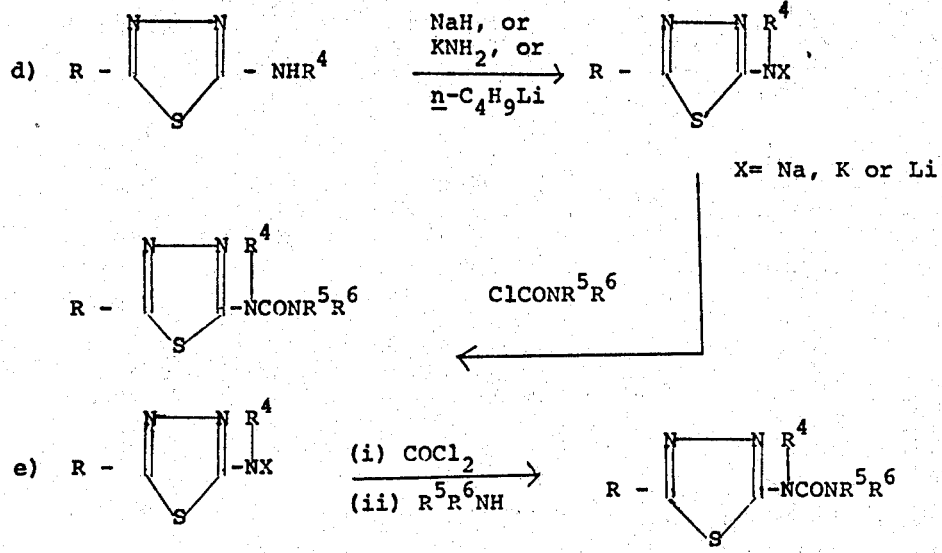

can be prepared by one or more of the synthesis routes set forth below. The type of product desired will determine the particular synthesis route to be employed.

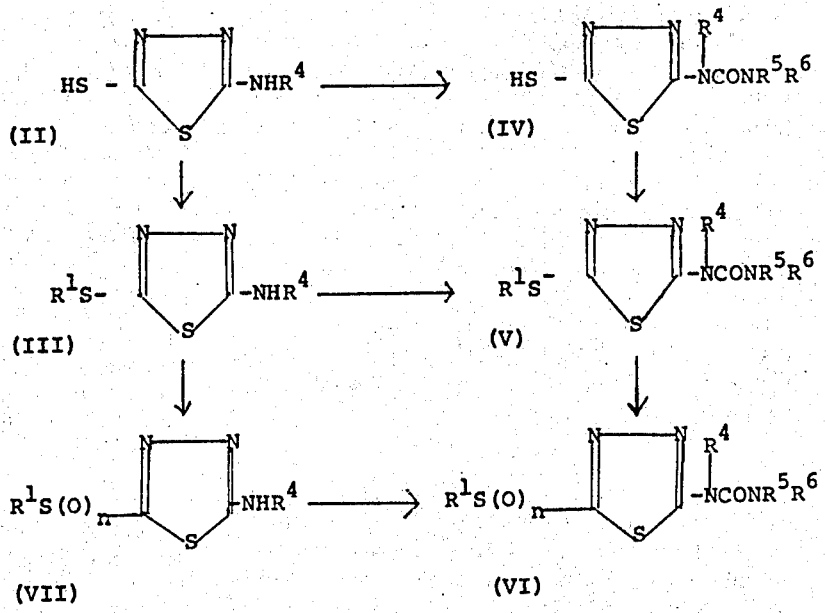

$n=1$ or $2$

The intermediate compositions corresponding to Structure (II) are synthesized by methods known in the art. For example, such methods are generally taught in publications such as *The Chemistry of Heterocyclic Compounds*, V. 4, L. L. Bambas, Interscience Publishers, Inc., New York, 1952 and Petrow et al., *J. Chem. Soc.* 1508 (1958). The intermediate compounds having the Structure (III) and (V) may be synthesized from compounds (II) and (IV) by known methods, e.g. reacting compounds (II) and (IV) with alkyl halides and dialkyl sulfates in the presence of a base such as potassium carbonate, sodium hydroxide, potassium hydroxide and the like.

Compounds having the ureido moieties, as shown above, may be synthesized by the several reactions a) through (e), already set forth hereinabove, and which are known in the art. It is understood that the method employed will depend upon the particular intermediate selected for producing the corresponding intermediate or desired final product.

The alkylmercapto compounds of structure (V) may be oxidized to the corresponding sulfones of structures (VI) and (VII) by oxidizing reagents such as chlorineacetic acid, chlorine-ferric chloride, potassium permanganate, hydrogen peroxide-acetic acid and the like. By careful control of oxidizing conditions, the sulfoxides of structures (VI) and (VII) are also prepared.

The following examples are illustrative of the methods of preparation of various compounds for use in the novel herbicidal method of this invention.

EXAMPLE 1

A mixture containing 30 g. of 2-(N-methylamino)-5-mercapto-1,3,4-thiadiazole and 11.60 g. of methyl isocyanate in 250 ml. of benzene was refluxed in a 500 ml. flask for a period of about 2 hours. The reaction product mixture was cooled and filtered to obtain 40 g. of a product having a melting point of about 162°–164°C., and identified as 1,3-dimethyl-3-(5-mercapto-1,3,4-thiadiazol-2-yl)urea.

Following the same general procedure of Example 1, and using suitable starting reactants, additional compounds were prepared.

A. Methyl isocyanate was allowed to react with 2-ethylimino-5-trifluoromethyl-$\Delta^4$-1,3,4-thiadiazoline to yield 1-methyl-3-ethyl-3-(5-trifluormethyl-1,3,4-thiadiazol-2-yl)urea, having a melting point of about 130°–132°C.

B. Methyl isocyanate was allowed to react with 2-(N-methylamino)-5-butylmercapto-1,3,4-thiadiazole to yield 1,3-dimethyl-2-(5-butylmercapto-1,3,4-thiadiazole-2-yl)urea, having a melting point of about 63°–65°C.

C. Methyl isocyanate was allowed to react with 2-amino-5-difluoromethyl-1,3,4-thiadiazole to yield 1-methyl-3-(5-difluoromethyl-1,3,4-thiadiazol-2-yl)urea, having a melting point of about 198°–200°C.

EXAMPLE 2

A mixture containing 5 g. of 1,3-dimethyl-3-(5-mercapto-1,3,4-thiadiazol-2-yl)urea, 3.7 g. of methyl iodide, and 1.7 g. of anhydrous potassium carbonate in 50 ml. of N,N-dimethylformamide, was stirred for about 15 hours at a temperature of about 70°C. The resulting clear reaction product mixture was concentrated under vacuum to a solid, which solid, on recrystallization from ethyl acetate, yielded a product identified as 1,3-dimethyl-3-(5-methylmercapto-1,3,4-thiadiazol-2-yl)urea, having a melting point of about 154°–156°C.

EXAMPLE 3

To a suspension of 5 g. of 1,3-dimethyl-3-(5-methylmercapto-1,3,4-thiadiazol-2-yl)urea in 50 ml. of acetic acid was added, dropwise and with stirring, an aqueous solution of potassium permanganate (7.3 g. in 100 ml. of water), said reaction mixture being cooled in an ice water bath. The resulting mixture was stirred for about 15 hours at room temperature after which time sodium bisulfite was added until the mixture became colorless. The solid product was filtered off, and was recrystallized from methanol to yield a product identified as 1,3-dimethyl-3-(5-methylsulfonyl-1,3,4-thiadiazol-2-yl)urea, having a melting point of about 182°–183°C.

EXAMPLE 4

In a three-necked round-bottom flask equipped with a mechanical stirring means and bubbling tube were placed 35.9 g. of 1,3-dimethyl-3-(5-butylmercapto-1,3,4-thiadiazol-2-yl)urea and 5 g. of ferric chloride hexahydrate in 500 ml. of water. The mixture was cooled to 5°C. and a steady stream of chlorine was bubbled through the mixture for about 20 minutes while maintaining the temperature at 7°–9°C. Nitrogen was subsequently bubbled through the mixture to remove excess chlorine. The reaction product mixture was filtered and the solid product recrystallized from aqueous methanol to provide a product identified as 1,3-dimethyl-3-(5-butylsulfonyl-1,3,4-thiadiazol-2-yl)urea, having a melting point of about 123°–124°C.

EXAMPLE 5

To a stirred solution containing 10 g. of N,N'-carbonyldiimidazole in 200 ml. of dry tetrahydrofuran was added 9.1 g. of 2-amino-5-methylmercapto-1,3,4-thiadiazole, the mixture being stirred for an additional 30 minutes under a nitrogen atmosphere and subsequently refluxed. The reaction mixture was cooled to room temperature and 18.7 g. of triethylamine was added followed by 18.0 g. of dimethyl hydroxylamine hydrochloride. After stirring for 15 minutes, the reaction product mixture was poured into an ice and water mixture and extracted with ethyl acetate. The ethyl acetate extract was dried over anhydrous sodium sulfate and subsequently concentrated under vacuum to a residual oil which solidified on standing. The solid material was recrystallized from methanol to yield a crystalline product which was identified as 1-methyl-1-methoxy-3-(5-methylmercapto-1,3,4-thiadiazol-2-yl)urea, having a melting point of about 97°–100°C.

Following the same general procedure of Example 5, and using suitable starting materials, the following compound was prepared:

A. 1-Methoxy-1-methyl-3-(5-t-butyl-1,3,4-thiadiazol-2-yl)urea, having a melting point of about 113°–115°C.

EXAMPLE 6

To a stirred solution containing 10.1 g. of 1-methyl-1-methoxy-3-(5-methylmercapto-1,3,4-thiadiazol-2-yl)urea and 50 g. of glacial acetic acid, heated to 85°–90°C., was added, over a period of about 15 minutes, 14.5 g. of 30 percent hydrogen peroxide. The temperature was maintained for an additional period of 1 hour and the mixture was then cooled to room temperature. The cooled reaction product mixture was poured into an ice and water mixture and extracted with ethyl acetate. The ethyl acetate extract was dried over anhydrous sodium sulfate and concentrated under vacuum to yield a product identified as 1-methyl-1-methoxy-3-(5-methylsulfonyl-1,3,4-thiadiazol-2-yl)urea, having a melting point of about 146°–148°C.

EXAMPLE 7

To a well-stirred mixture of 20 g. of 2-amino 5-methylmercapto-1,3,4-thiadiazole and 18.4 g. of N-methyl-N-butylcarbamoyl chloride, in dimethylformamide, which mixture had been cooled to about 5°C., was slowly added 4.7 g. of sodium hydride. The reaction mixture was slowly poured into an ice and water mixture and the total mixture extracted with chloroform. The chloroform extract was concentrated under vacuum to yield a material which, on recrystallization from ethanol, provided a product identified as 1-butyl-1-methyl-3-(5-methylmercapto-1,3,4-thiadiazol-2-yl)urea, having a melting point of about 93°–94°C.

Following the same general procedure of Example 7, and using suitable principal reactants, the following compound was prepared:
  A. 1,1,3-Trimethyl-3-(5-t-butyl-1,3,4-thiadiazol-2-yl)urea, which was isolated as an oil and identified by NMR.

EXAMPLE 8

A stirred mixture, containing 9.3 g. of 1-butyl-1-methyl-3-(5-methylmercapto-1,3,4-thiadiazol-2-yl)urea and 5.0 g. of ferric chloride in 400 ml. of water, was cooled to about 5°C., and chlorine gas was bubbled through the mixture for about 30 minutes. Nitrogen was then bubbled through the mixture to remove excess chlorine and the precipitate which formed was separated from the solution by filtration. The precipitate was recrystallized from ethyl alcohol to yield a product which was identified as 1-butyl-1-methyl-3-(5-methylsulfonyl-1,3,4-thiadiazol-2-yl)urea, having a melting point of about 125°–126°C.

EXAMPLE 9

A mixture of 8.4 g. (0.05 moles) of 2-amino-5-trifluoromethyl-1,3,4-thiadiazole and 5 g. (0.056 moles) of allyl isocyanate in anhydrous ethyl acetate was refluxed for 1½ hours. Petroleum ether (b.p. 30°–60°C.) was added to the partially cooled reaction product mixture. On further cooling, a solid material separated, which was filtered off and recrystallized from methanol. This product (m.p. about 156°–158°C.) was identified as 1-allyl-3-(5-trifluoromethyl-1,3,4-thiadiazol-2-yl)urea.

Following the same general procedure of Example 9, and using suitable starting reactants, additional compounds were prepared, as follows:
  A. Methyl isocyanate was allowed to react with 2-amino-5-trifluoromethyl-1,3,4-thiadiazole to yield 1-methyl-3-(5-trifluoromethyl-1,3,4-thiadiazol-2-yl)urea, having a melting point of about 192°–194°C.
  B. Methyl isocyanate was allowed to react with 2-methylimino-5-trifluoromethyl-$\Delta^4$-1,3,4-thiadiazoline to yield 1,3-dimethyl-3-(5-trifluoromethyl-1,3,4-thiadiazol-2-yl)urea, having a melting point of about 137°–138°C.
  C. Methyl isocyanate was allowed to react with 2-methylimino-5-tert.-butyl-1,3,4-thiadiazoline to yield 1,3-dimethyl-3-(5-tert.-butyl-1,3,4-thiadiazol-2yl)urea, having a melting point of about 159°–162°C.

EXAMPLE 10

To a vigorously stirred solution of 10.5 g. (0.062 moles) of 2-amino-5-trifluoromethyl-1,3,4-thiadiazole in freshly distilled tetrahydrofuran (distilled from lithium aluminum hydride), cooled to 0°C., was added, dropwise, n-butyllithium in n-hexane (60 ml. of 1.2 M. solution). After complete addition of the butyllithium, the reaction mixture was refluxed for 2 hours, cooled again to 0°C., and N,N-dimethylcarbamoyl chloride (6.7 g.) (0.063 moles) added dropwise. The reaction product mixture was then stirred at room temperature, for a prolonged period, refluxed for 3 hours, and washed with a saturated aqueous ammonium sulfate solution. The organic layer was separated and dried over anhydrous sodium sulfate. The drying agent was filtered off and the organic solution concentrated to a gum, which was dissolved in methanol. Addition of a little water to the methanol yielded a quantity of oil which was removed by filtration through a Celite pad. Addition of more water to the filtrate gave a solid product which, after recrystallization from aqueous methanol, was identified as 1,1-dimethyl-3-(5-trifluoromethyl-1,3,4-thiadiazol-2-yl)urea, having a melting point of about 151°–153°C.

EXAMPLE 11

A urea compound was prepared in accordance with the reaction as hereinbefore described in reaction sequence b): To toluene (1,100 ml.), contained in a 2 l. round bottom flask equipped with a stirrer and a Dry Ice condenser, was added 62 g. of phosgene at room temperature. When addition to the phosgene was complete, 7 g. of boron trifluoride-etherate was added, followed by 45 g. of solid 5-chlorodifluoromethyl-2-methylamino-1,3,4-thiadiazole. The reaction mixture was then heated to 50°–60°C. and maintained at this temperature for 3 hours. It was then cooled in an ice bath and gaseous dimethylamine added at such a rate that the temperature was maintained at 40°–50°C. The dimethylamine was added until no further exotherm was observed. Then the reaction product mixture was filtered and the filtrate washed successively with 6N hydrochloric acid (2×250 ml.) and water (2×250 ml.), and dried over anhydrous sodium sulfate. The drying agent was filtered off, the toluene solution concentrated under vacuum and the residue recrystallized from petroleum ether to give material having a melting point of about 43°–45°C. The material was identified as 1,1,3-trimethyl-3-(5-chlorodifluoromethyl-1,3,4-thiadiazol-2-yl)urea.

Additional compounds prepared according to the procedures set forth hereinabove include the following:

| Example | R | $R^4$ | $R^5$ | $R^6$ | Melting Point, °C. |
|---|---|---|---|---|---|
| 12 | $CF_3$ | $CH_3$ | $CH_3$ | $OCH_3$ | oil[1] |
| 13 | $CHF_2$ | $CH_3$ | $CH_3$ | $OCH_3$ | 70–73 |
| 14 | $CF_3$ | H | $CH_3$ | $OCH_3$ | 104–106 |
| 15 | $CHF_2$ | H | $CH_3$ | $OCH_3$ | 137–138 |
| 16 | $C_2F_5$ | $CH_3$ | $CH_3$ | $OCH_3$ | oil[2] |
| 17 | $CClF_2$ | $CH_3$ | $CH_3$ | $OCH_3$ | oil[3] |
| 18 | $ClCH_2-C(CH_3)_2$ | $CH_3$ | H | $CH_3$ | 143–145 |

[1]Analysis:   Calculated: C, 31.14; H, 3.36; N, 20.75
             Found: C, 31.19; H, 3.49; N, 20.37
[2]Analysis:   Calculated: C, 30.03; H, 2.84; N, 17.51
             Found: C, 29.71; H, 2.76; N, 17.27
[3]Analysis:   Calculated: C, 29.29; H, 3.17; N, 19.52
             Found: C, 29.78; H, 3.20; N, 19.36

The compounds wherein

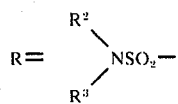

can be synthesized by one or more of the reaction sequences previously set forth, as well as by those taught by Cebalo, U.S. Pat. No. 3,726,892 (Apr. 10, 1973), the disclosures of which patent are hereby incorporated into and made a part of this specification.

EXAMPLE 19

Following the same general procedure of Example 7, 2-methylamino-1,3,4-thiadiazole-5-N,N-dimethylsulfonamide was allowed to react with N,N-dimethylcarbamoyl chloride to yield 1,1,3-trimethyl-3-(5-dimethylsulfamoyl-1,3,4-thiadiazol-2-yl)urea, having a melting point of about 101°–103°C.

A. 2-Ethylamino-1,3,4-thiadiazole-5-N,N-dimethylsulfonamide was allowed to react with N,N-dimethylcarbamoyl chloride to yield 1,1-dimethyl-3-ethyl-3-(5-dimethylsulfamoyl-1,3,4-thiadiazol-2-yl)urea, having a melting point of about 75°–77°C.

The compounds usable in the invention, which compounds correspond to generic formula (I), wherein $R^4$ is hydrogen, (see I, below) form metal and ammonium salts (substituted or unsubstituted) corresponding to the structure (Ia) below. For polyvalent metals, the salt compounds are chelate in character. The alkali metal and ammonium salts provide highly desirable properties such as water solubility when employed for use in agricultural applications. Preparation of these salts is described in U.S. Pat. No. 3,565,901 (Feb. 23, 1971), which description is hereby incorporated herein and made a part of this disclosure. Furthermore, alkali metal salts are found to react with reactive halogen compounds, i.e., alkyl halides or alkyl sulfates, to produce derivatives as shown in (VIII) and (IX) below:

Compounds possessing the structures of generic formula (I) may be used in the herbicidal method of the present invention. The compounds may be used in various states of purity, ranging, for example, from crystals to a technical crude grade. Suitable solvents for these compounds include alcohols, aqueous alcohol solutions, and ketones, including acetone and methyl isobutyl ketone.

Each compound to be used in the herbicidal method of this invention may be prepared as a simple solution in an appropriate solvent in which the compound is completely soluble at the desired concentration. Appropriate solvents include water, alcohols, acetone, aqueous alcohol and acetone, and other organic solvents. These simple solutions may be further modified by the addition of various surfactants, emulsifying or dispersing agents, colorants, odorants, antifoaming agents, or other herbicides or herbicidal oils which supplement or synergize the activity of the herbicides used in the invention, or other adjuvants for any given application where deemed desirable. Compounds usable in the herbicidal method of the invention may also be formulated in various other types of formulations commonly recognized by those skilled in the art of agricultural chemicals. These formulations include, for example, compositions containing the active ingredient as granules of relatively large particle size, as powder dusts, as wettable powders, as emulsifiable concentrates, or as a constituent part of any other known type of formulation commonly utilized by those skilled in the art. Such formulations include the adjuvants and carriers normally employed for facilitating the dispersion of active ingredients for agricultural and industrial applications of phytotoxicants. These formulations may contain as little as 0.25 percent or as much as 95 percent or more by weight of the active ingredient.

Dust formulations are prepared by mixing the active thiadiazole ingredient with finely-divided solids which act as dispersants and carriers for the phytotoxicant in applying it to the locus of application for vegetation control. Typical solids which may be utilized in preparing dust formulations of the active ingredients of the

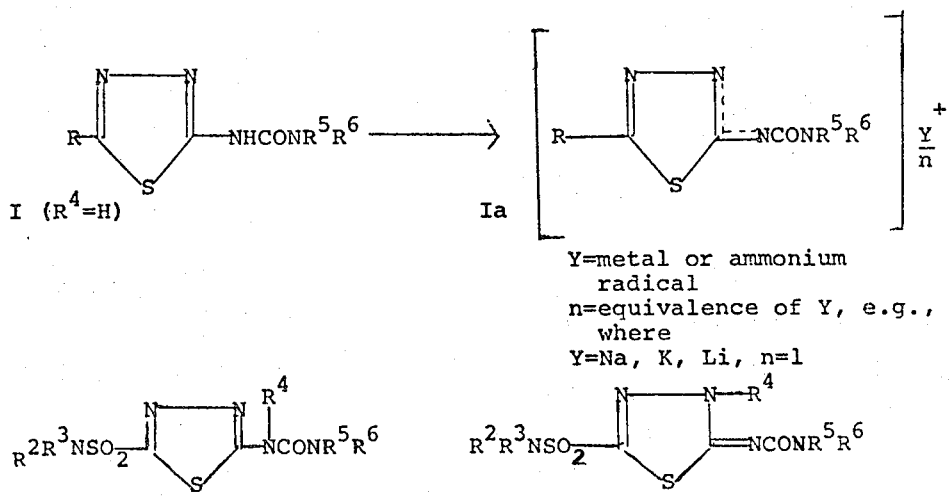

invention include talc, hydrated sodium silico aluminates, hydrated silicon dioxide, kieselguhr, finely-divided clay, fullers, earth, or other common organic or inorganic solids. Solids utilized in preparing dust formulations of the active ingredient normally have a particle size of 50 microns or less. The active ingredient of these dust formulations is present commonly in as little as 0.25 percent to as much as 30 percent or more by weight of the composition.

Granular formulations of the active ingredients are prepared by impregnating or adsorbing the toxicant on or into relatively coarse particles of inert solids such as sand, attapulgite clay, gypsum, corn cobs or other inorganic or organic solids. The active ingredient of these granular formulations is commonly present in from about 1 percent to as much as 20 percent or more by weight of the composition.

Wettable powder formulations are solid compositions of matter wherein the active ingredient is absorbed or adsorbed in or on a sorptive carrier such as finely-divided clay, talc, gypsum, lime, wood flour, fullers' earth, kieselguhr, or the like. These formulations preferably are made to contain from about 50 percent to about 80 percent of active ingredient. These wettable powder formulations commonly contain a small amount of a wetting, dispersing, or emulsifying agent to facilitate dispersion in water or other liquid carrier utilized to distribute the phytotoxicant to the locus of desired vegetation control. Suitable surfactants, emulsifying agents, and dispersants include both anionic and nonionic substances such as alkyl ether sodium sulfate and alkyl aryl polyethoxyethanols, sodium N-methyl-N-palmitoyltaurate, the oleic acid ester of sodium isethionate, sodium lignosulfonate, alkyl aryl sulfonates, highly polymerized naphthalenesulfonate, alkyl aryl polyether alcohols, sodium lauryl sulfate, and the like.

Emulsifiable concentrate formulations are homogeneous liquid or paste compositions containing the active ingredient. Such compositions will disperse in water or other liquid carrier to facilitate application of the phytotoxicant to the locus of desired vegetation control. Such emulsifiable concentrate formulations of the active ingredients may contain only the active ingredient with a liquid or solid emulsifying agent, or may contain other relatively non-volatile organic solvents such as isophorane, dioxane, heavy aromatic napthas, xylene, or dimethylformamide. The active ingredient in such formulations commonly comprises from about 10 percent to about 70 percent by weight of the phytotoxicant composition.

The novel process of this invention comprises treating a soil area or locus wherein wheat has been grown and harvested with a compound of the formula set forth hereinabove. Thus, the herbicidally-active compound or compositions containing the herbicidally-active compound are sprayed, dusted, or spread by other methods well known to the art onto the particular area at the rate of from about 0.5 to about 2 pounds per acre of the herbicidally-active ingredient. For most field applications, it is preferred to spray the herbicidal composition at the rate of from about 0.5 to about 1.0 pound of active ingredient per acre.

The general herbicidal activity of representative compounds coming within the scope of generic formula I supra is illustrated by the following greenhouse trials, wherein compounds were evaluated as both preemergent and postemergent herbicides against a number of plant species, including both weeds and crops, using the following procedure:

A soil was prepared consisting of 1 part masonry sand and 1 part shredded topsoil blended together in a cement mixer. Galvanized flats measuring 21.5 × 31.5 × 8 cm. were filled with 1 gal. of this soil mixture and the soil patted down with a bench brush until level. Two and one-half grams of soluble fertilizer (23-19-17) were applied to each flat during the initial watering. The seeds were planted in rows parallel to the long axis, one species per half row. The 20 plant species used, numbered consecutively for identification purposes in Chart 1, and the approximate number of seeds planted were as follows:

1. Corn (*Zea mays*) 4
2. Cotton (*Gossypium hirsutum*) 6
3. Soybean (*Glycine max*) 6
4. Wheat (*Triticum aestivum*) 40
5. Alfalfa (*Medicago sativa*) 175
6. Sugar beet (*Beta vulgaris*) 25
7. Rice (*Oryza sativa*) 35
8. Cucumber (*Cucumis sativus*) 8
9. Tomato (*Lycopersicon esculentum*) 45
10. Barnyard grass (*Echinochloa crusgalli*) 50
11. Lambsquarter (*Chenopodium album*) 100
12. Cocklebur (*Xanthium pennsylvanicum*) 6
13. Large crabgrass (*Digitaria sanguinalis*) 250
14. Mustard (*Brassica sp.*) 125
15. Pigweed (*Amaranthus retroflexus*) 250
16. Foxtail millet (*Setaria italica*) 100
17. Wild Oat (*Avena fatua*) 25
18. Velvetleaf (*Abutilon theophrasti*) 50
19. Morning glory (*Ipomoea purpurea*) 20
20. Zinnia (*Zinnia elegans*) 20

Two flats (10 species each) were used for each application rate of each herbicidally-active compound.

In assaying the effect of the compositions as preemergent herbicides, a flat prepared as above, either on the day of planting or on the next day, was placed in a chamber with air exhaust. The compounds were formulated for test as follows: Each compound was dissolved in acetone and ethanol (1:1 ratio) containing a small amount of a surfactant blend. One suitable surfactant blend contains 3 parts of the calcium salt of myristylbenzene sulfonic acid to one part of the oleate ester of a polyoxyethylene glycol (Molecular Weight = 350), while another suitable surfactant blend contains 7 parts of the calcium salt of laurylphenolsulfonic acid to 3 parts of mono- and di-resin acid esters of polyoxyethylene glycol (M.W.=500). The volume of solvent was 10 percent of the final spray volume. The solution was then diluted with deionized water to 12.5 ml. and applied to each flat with a modified De Vilbiss atomizer hooked to an air source, either on the day of planting or the succeeding day. The concentration of this solution provides test material at the application rate of 8 lb./A. Serial dilution of this particular solution was then accomplished to provide suitable concentrations of solutions to effect application of the test compounds at the other rates desired for study.

Injury ratings and observations as to type of injury were made 11 to 12 days after treatment. The injury rating scale used was as follows:

0 -- no injury
1 -- slight injury
2 -- moderate injury
3 -- severe injury
4 -- death When more than one determination was carried out, an average value was calculated for the injury rating.

The results of the above trials are set forth in Chart 1 which follows. In the Chart, column 1 identifies the compound (Cpd.) under test; column 2, the rate in lbs./A. at which the compound was applied to the test flat; and the remaining columns, the injury rating for the particular plant seeds or seedlings, the species being identified by number.

The test compounds are identified by a letter or combination of letters according to the following list:

A  1-(5-Dimethylsulfamoyl-1,3,4-thiadiazol-2-yl)-1,3,3-trimethylurea
B  3-(5-Dimethylsulfamoyl-1,3,4-thiadiazol-2-yl)-1-methoxy-1-methylurea
C  1-(5-Dimethylsulfamoyl-1,3,4-thiadiazol-2-yl)-3-methylurea
D  1-(5-Dimethylsulfamoyl-1,3,4-thiadiazol-2-yl)-1,3-dimethylurea
E  1-[5-(2-Chloro-N-methylethylsulfamoyl)-1,3,4-thiadiazol-2-yl]-1,3,3-trimethylurea
F  1-(5-t-Butyl-1,3,4-thiadiazol-2-yl)-1,3-dimethylurea
G  1,3-Dimethyl-1-(5-trifluoromethyl)-1,3,4-thiadiazol-2-yl)urea
H  1-[5-(2,2-Dimethoxy-N-methylethylsulfamoyl)-1,3,4-thiadiazol-2-yl]-1,3,3-trimethylurea
I  1-(5-Dimethylsulfamoyl-1,3,4-thiadiazol-2-yl)-3-methylurea, potassium salt
J  1-[5-(N-Methoxy-N-methylsulfamoyl)-1,3,4-thiadiazol-2-yl]-1,3,3-trimethylurea
K  1,1,3-Trimethyl-3-[5-(N-methyl-sec.-butylsulfamoyl)-1,3,4-thiadiazol-2-yl]urea
L  1-(5-Dimethylsulfamoyl-1,3,4-thiadiazol-2-yl)-1-ethyl-3-methylurea
M  1-[5-(Dimethylsulfamoyl)-1,3,4-thiadiazol-2-yl]-1-ethyl-3,3-dimethylurea
N  1-Methyl-3-[5-(trifluoromethyl)-1,3,4-thiadiazol-2-yl]urea
O  1-(5-Chlorodifluoromethyl-1,3,4-thiadiazol-2-yl)-1,3-dimethylurea
P  1-Methyl-3-[5-(1,1,2,2-tetrafluoroethyl)-1,3,4-thiadiazol-2-yl]urea
Q  1-(5-Difluoromethyl-1,3,4-thiadiazol-2-yl)-3-methylurea
R  1,1,3-Trimethyl-3-(5-trifluoromethyl-1,3,4-thiadiazol-2-yl)urea
S  1,3-Dimethyl-1-[5-(1,1,2,2-tetrafluoroethyl)-1,3,4-thiadiazol-2-yl]urea
T  1,1,3-Trimethyl-1-[5-(1,1,2,2-tetrafluoroethyl)-1,3,4-thiadiazol-2-yl]urea
U  1,1,3-Trimethyl-3-[5-(pentafluoroethyl)-1,3,4-thiadiazol-2-yl]urea
V  1-(5-t-Butyl-1,3,4-thiadiazol-2-yl)-1-ethyl-3-methylurea
W  1,3-Dimethyl-1-[5-(pentafluoroethyl)-1,3,4-thiadiazol-2-yl]urea
X  1-(5-Chlorodifluoromethyl-1,3,4-thiadiazol-2-yl)-1,3,3-trimethylurea
Y  1-(5-Isopropyl-1,3,4-thiadiazol-2-yl)-1,3-dimethylurea
Z  1-[5-(t-Butyl)-1,3,4-thiadiazol-2-yl]-3-methylurea
AA  1-(5-t-Butyl-1,3,4-thiadiazol-2-yl)-1,3,3-trimethylurea
AB  1-(5-Isopropyl-1,3,4-thiadiazol-2-yl)-1,3,3-trimethylurea
AC  1-[5-(1-Cyano-1-methylethyl)-1,3,4-thiadiazol-2-yl]-1,3-dimethylurea
AD  1-(5-t-Butyl-1,3,4-thiadiazol-2-yl)-3-methoxy-3-methylurea
AE  1-[5-(2-Chloro-1,1-dimethylethyl)-1,3,4-thiadiazol-2-yl]-1,3-dimethylurea
AF  3-[5-(2-Chloro-1,1-dimethylethyl)-1,3,4-thiadiazol-2-yl]-1-methoxy-1-methylurea
AG  1-[5-(2-Chloro-1,1-dimethylethyl)-1,3,4-thiadiazol-2-yl]-1,3,3-trimethylurea
AH  1,3-Dimethyl-1-(5-methylsulfonyl-1,3,4-thiadiazol-2-yl)urea
AI  1-(5-Ethylsulfonyl-1,3,4-thiadiazol-2-yl)-1,3-dimethylurea
AJ  1-[5-(Sec. butylsulfonyl)-1,3,4-thiadiazol-2-yl]-1,3-dimethylurea

CHART 1

| Cpd. | Appln. Rate Lb./A. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| A | 0.2 | 1 | 1 | 1 | 1 | 2 | 4 | 1 | 1 | 1 | 1 | 2 | 1 | 1 | 3 | 1 | 1 | 1 | 1 | 1 | 1 |
|   | 0.5 | 1 | 1 | 1 | 1.5 | 2.5 | 3.5 | 1 | 2 | 2.5 | 3 | 2.5 | 2 | 2.5 | 5 | 3 | 3 | 2.5 | 3 | 3 | 4 |
|   | 1 | 2.5 | 2.5 | 1.5 | 2.5 | 4.5 | 5 | 1.5 | 5 | 4 | 3 | 3.5 | 1.5 | 3.5 | 4.5 | 5 | 4 | 3 | 4 | 5 | 5 |
|   | 2 | 3 | 3 | 2 | 3 | 4 | 5 | 1 | 5 | 4 | 3 | 2 | — | 3 | 5 | 4 | 4 | 3 | 4 | 4 | 5 |
|   | 4 | 5 | — | — | — | — | — | — | — | — | — | — | — | 4 | — | 4 | 5 | — | 4 | 5 | 5 |
| B | 0.2 | 1 | 1 | 1 | 1 | 1 | 4 | 1 | 1 | 1 | 1 | 1 | 1 | 1 | 1 | 1 | 1 | 1 | 1 | 1 | 2 |
|   | 0.5 | 1 | 1 | 1 | 1 | 1.5 | 2.5 | 1 | 2 | 1.5 | 2.5 | 3.5 | 3 | 1 | 4.5 | 3.5 | 2.5 | 1.5 | 1 | 2 | 1.5 |
|   | 1 | 2 | 4 | 3 | 2.5 | 4 | 3 | 2 | 3 | 4 | 4 | 5 | 5 | 3 | 5 | 5 | 4 | 2 | 1 | 3 | 4 |
|   | 2 | 2.5 | 3 | 3.5 | 3.5 | 5 | 4 | 2.5 | 4 | 4 | 3.5 | 4.5 | 3.5 | 3.5 | 5 | 4.5 | 4 | 3 | 5 | 2.5 | 4.5 |
|   | 4 | 5 | 5 | 5 | 5 | 5 | 5 | 5 | 5 | 5 | 5 | 5 | 5 | 5 | 5 | 5 | 5 | 5 | 5 | 5 | 5 |
| C | 0.5 | 1.5 | 2.5 | 2.5 | 3 | 2.5 | 3 | 2 | 2 | 2 | 2.5 | 2.5 | 2 | 3.5 | 2.5 | 3.5 | 2.5 | 2.5 | 1.5 | 1 | 1.5 |
|   | 1 | 3 | 3 | 3 | 3 | 3 | 4 | 2.5 | 3.5 | 3 | 3 | 3 | 3 | 4 | 3.5 | 3 | 4 | 3 | 2 | 1 | 3 |
|   | 2 | 3 | 3 | 3 | 3.5 | 3.5 | 4.5 | 2.5 | 3.5 | 4 | 3.5 | 2.5 | 3 | 4 | 4 | 3.5 | 4 | 3 | 3.5 | 1.5 | 3.5 |
| D | 0.5 | 1 | 1 | 1 | 1 | 3 | 2 | 1 | 2 | 2 | 1 | — | 1 | 4 | 2 | — | 1 | 2 | 3 | 1 | 1 |
|   | 1 | 1 | 1 | 1 | 2.5 | 3.5 | 4.5 | 1 | 4 | 4.5 | 2 | 4 | 1.5 | 3.5 | 3.5 | 4 | 3 | 2.5 | 4 | 2 | 4 |
|   | 2 | 3 | 2 | 1.5 | 2.5 | 4 | 4.5 | 1.5 | 4 | 4 | 2.5 | 4 | 2 | 3.5 | 3.5 | 4 | 3 | 3.5 | 4.5 | 3 | 4.5 |
|   | 4 | 4 | 2 | 4 | 3 | 5 | 4 | 2 | 4 | 4 | 4 | 3 | 4 | 5 | 4 | 4 | 4 | 5 | 5 | 4 |  |
| E | 0.2 | 1 | 1 | 1 | 1 | 1 | 1 | 1 | 1 | 1 | 1 | 1 | 1 | 1 | 1 | 1 | 1 | 1 | 1 | 1 | 1 |
|   | 0.5 | 1 | 1 | 1 | 1 | 2.5 | 3.5 | 1 | 2 | 2 | 1 | 1 | 1 | 1 | 2.5 | 2 | 1.5 | 2 | 2.5 | 1.5 | 1.5 |
|   | 1 | 1.5 | 1.5 | 1 | 1 | 3.5 | 3.5 | 1 | 2.5 | 3 | 3 | 3.5 | 1.5 | 3 | 2.5 | 3.5 | 3.5 | 3 | 5 | 3.5 | 3.5 |
|   | 2 | 3 | 2 | 1 | 2 | 5 | 4 | 1 | 4 | 2 | 3 | 3 | 4 | 2 | 3 | 3 | 5 | 5 | 2 | 3 |  |
| F | 0.2 | 0.5 | 0.5 | 0 | 1 | 2.5 | 2.5 | 0.5 | 2 | 1.5 | 2 | 1 | 2 | 3 | 3 | 2 | 1.5 | 2 | — | 1.5 | 3.5 |
|   | 0.5 | 0.6 | 3 | 1.3 | 1 | 2.3 | 3 | 0.3 | 3.6 | 3.3 | 2.6 | 2.6 | 3 | 3.3 | 4 | 3.6 | 3 | 3 | — | 2.3 | 4 |
|   | 1.0 | 2 | 3.3 | 3.3 | 2.6 | 3.6 | 3.6 | 1.6 | 4 | 4 | 3.6 | 3 | 4 | 4 | 4 | 4 | 3.6 | 3 | 3 | 4 |  |
|   | 2.0 | 3 | 4 | 2 | 3 | 4 | 3.5 | 2 | 4 | 4 | 3.5 | 3 | 3 | 3.5 | 4 | 4 | 4 | 3.5 | 4 | 3.5 | 4 |
|   | 4.0 | 4 | 4 | 4 | 4 | 4 | 4 | 4 | 4 | 4 | 4 | 3 | 4 | 4 | 4 | 4 | 4 | 4 | 3 | 4 |  |
| G | 0.2 | 0.3 | 0 | 0 | 0.3 | 1.5 | 2.5 | 0 | 1 | 2 | 0.5 | 2.5 | 0.5 | 2 | 3 | 1.5 | 1.5 | 0.5 | — | 0.5 | 1 |
|   | 0.5 | 0.5 | 1 | 0.5 | 1 | 2 | 3 | 1 | 3.5 | 3.5 | 3 | 3 | 1.5 | 3 | 4 | 3 | 2 | 2 | — | 2 | 3 |
|   | 1.0 | 2 | 4 | 4 | 4 | 4 | 3 | 4 | 4 | 4 | 4 | 3 | 4 | 4 | 4 | 4 | 4 | 4 | 3 | 4 |  |
|   | 2.0 | 4 | 4 | 4 | 4 | 4 | 4 | 3 | 4 | 4 | 4 | 3 | 4 | 4 | 4 | 4 | 4 | 4 | 3 | 3 | 4 |

3,972,706

CHART 1-continued

| Cpd. | Appln. Rate Lb./A. | \multicolumn{20}{c}{Injury Rating} |||||||||||||||||||
|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| | 4.0 | 4 | 4 | 4 | 4 | 4 | 4 | 3 | 4 | 4 | 3 | 4 | 4 | 4 | 4 | 4 | 4 | 4 | 3 | 4 | |
| H | 0.2 | 1 | 1 | 1 | 1 | 1 | 1 | 1 | 1 | 1 | 1 | 1 | 1 | 1 | 1 | 1 | 1 | 1 | 1 | 1 | 1 |
| | 0.5 | 1 | 1 | 1 | 1.5 | 3 | 3 | 1.5 | 2 | 1.5 | 1 | 1 | 1 | 1.5 | 2.5 | 1 | 1.5 | 1.5 | 3.5 | 1.5 | 1.5 |
| | 1 | 1.5 | 1 | 1 | 2 | 4 | 2.5 | 1.5 | 3.5 | 2 | 2.5 | 4 | 1.5 | 2.5 | 3.5 | 4 | 2.5 | 2.5 | 4 | 2.5 | 3 |
| | 2 | 4 | 5 | 3 | 3 | 5 | 4 | 3 | 5 | 4 | 2 | — | — | 3 | 3 | 2 | 4 | 5 | 5 | 3 | 3 |
| I | 0.5 | 1 | 1 | 1 | 1 | 1 | 2 | 1 | 1 | 1 | 2 | 2 | 2 | 2 | 1 | 3 | .3 | 1 | 1 | 2 | 1 |
| | 1 | 2 | 1 | 1.5 | 2 | 2.5 | 3.5 | 1.5 | 1.5 | 2 | 3 | 4 | 1.5 | 4.5 | 2.5 | 3.5 | 3.5 | 2 | 3 | 1 | 2.5 |
| | 2 | 3 | 3 | 3 | 2.5 | 3 | 4 | 2 | 3 | 4 | 4 | 4 | 3 | 5 | 4 | 4 | 5 | 3.5 | 4 | 2 | 4 |
| | 4 | 3 | 3 | 3 | 3 | 4 | 4 | 2 | 4 | 5 | 4 | 3 | 3 | 4 | 4 | 4 | 4 | 4 | 3 | 2 | 5 |
| J | 0.5 | 1 | 1 | 1 | 1 | 3 | 2 | 1 | 1 | 3 | 1 | 3 | — | 1 | 3 | 1 | 1 | 1 | 1 | 1 | 2 |
| | 1 | 2 | 1 | 1 | 1 | 3 | 4 | 1 | 1 | 3 | 1 | 4 | — | 2 | 3 | 3 | 2 | 2 | 3 | 2 | 3 |
| | 2 | 2 | 1 | 1 | 2 | 3 | 4 | 1 | 3 | 3 | 2 | 3 | — | 3 | 4 | 3 | 3 | 3 | 5 | 2 | 4 |
| K | 0.5 | 1 | 1 | 1 | 1 | 1 | 2 | 1 | 1 | 3 | 2 | 2 | — | 1 | 3 | 3 | 1 | 1 | 1 | 1 | 1 |
| | 1 | 1 | 1 | 1 | 2 | 2 | 2 | 1 | 2 | 4 | 2 | 2 | 1 | 2 | 3 | 3 | 3 | 1 | 2 | 2 | 4 |
| | 2 | 1 | 1 | 1 | 2 | 2 | 5 | 1 | 5 | 5 | 3 | 3 | 1 | 3 | 4 | 4 | 2 | 2 | 5 | 3 | 5 |
| L | 0.5 | 1 | 1 | 1 | 1 | 3 | 2 | 1 | 2 | 3 | 2 | 3 | 1 | 2 | 3 | 2 | 2 | 2 | 3 | 3 | 3 |
| | 1 | 2 | 1 | 2 | 2 | 3 | 2 | 2 | 2 | 3 | 2 | 3 | — | 3 | 2 | 3 | 4 | 3 | 4 | 1 | 2 |
| | 2 | 2 | 3 | 3 | 3 | 4 | 3 | 1 | 5 | 4 | 2 | 4 | 1 | 3 | 4 | 4 | 4 | 4 | 4 | 2 | 4 |
| M | 0.2 | 1 | 1 | 1 | 1 | 1 | 3 | 1 | 2 | 1 | 1 | — | 1 | 2 | 3 | — | 1 | 2 | 2 | 2 | 1 |
| | 1 | 1 | 1 | 2 | 1 | 1 | 3 | 1 | 2 | 1 | 2 | — | 1 | 2 | 3 | — | 2 | 4 | 3 | 2 | 2 |
| | 2 | 1 | 1 | 2 | 2 | 1 | 4 | 1 | 3 | 2 | 3 | — | 1 | 3 | 4 | — | 3 | 4 | 4 | 3 | 2 |
| N | 0.2 | 1 | 1 | 1 | 1 | 1 | 4 | 1 | 1 | 1 | 1 | 2 | 1 | 1 | 1 | 1 | 2 | 1 | — | 1 | 1 |
| | 0.5 | 1 | 1 | 1 | 2 | 3 | 3.5 | 1 | 2 | 2.5 | 2.5 | 3 | 2 | 2 | 3.5 | 2 | 3 | 1 | — | 1.5 | 3 |
| | 1 | 2 | 3 | 3 | 3 | 3 | 5 | 2 | 4 | 4 | 4 | 4 | 3.5 | 4 | 4 | 3 | 3 | 3 | 5 | 2 | 5 |
| | 2 | 3.5 | 4 | 4 | 4 | 4 | 5 | 3 | 5 | 5 | 4 | 4.5 | 4 | 4.5 | 5 | 4.5 | 4 | 4.5 | 5 | 3.5 | 5 |
| | 4 | 5 | 5 | 5 | 5 | 5 | 5 | 4 | 5 | 5 | 4 | 5 | 5 | 5 | 5 | 5 | 5 | 5 | 5 | 5 | 5 |
| O | 0.2 | 1 | 1 | 1 | 1 | 1 | 1 | 1 | 1 | 1 | 1 | 1 | 1 | 1 | 1 | 1 | 1 | 1 | 1 | 1 | 1 |
| | 0.5 | 1 | 1 | 1 | 1 | 1 | 1.5 | 3 | 1 | 1.5 | 1 | 1.5 | 3.5 | 1 | 3 | 3.5 | 1.5 | 2 | 4 | 1.5 | 1.5 |
| | 1 | 1 | 1 | 1 | 1 | 1 | 4 | 3 | 1 | 3 | 3 | 3 | 1 | 4 | 3 | 4 | 3 | 2 | 3 | 2 | 3 |
| | 2 | 2 | 1.5 | 1 | 2 | 4.5 | 4.5 | 1.5 | 4 | 5 | 3 | 3.5 | 1 | 4 | 4 | 4 | 4 | 4 | 4 | 2.5 | 4.5 |
| | 4 | 3 | 1 | 1 | 2 | 5 | 4 | 1 | 5 | 5 | 3 | 2 | — | 4 | 4 | 4 | 4 | 3 | 3 | 2 | 3 |
| P | 0.5 | 1 | 1 | 1 | 1 | 1 | 3 | 1 | 1 | 1 | 1 | 1 | 1 | 2 | 2 | 1 | 1 | 2 | 3 | 1 | 1 |
| | 1 | 1 | 1.5 | 1 | 1 | 1 | 3 | 1 | 1.5 | 2.5 | 2 | 4 | 1.5 | 3 | 3.5 | 4 | 3 | 2.5 | 4 | 2.5 | 1.5 |
| | 2 | 2 | 1 | 1 | 2 | 2 | 4.5 | 1 | 3.5 | 3 | 3 | 3 | 1 | 3 | 4.5 | 4 | 4 | 2.5 | 4 | 1 | 2 |
| | 4 | 3 | 2 | 2 | 3 | 4 | 5 | 1 | 5 | 4 | 3 | 4 | — | 4 | 4 | 4 | 4 | 4 | 4 | 2 | 4 |
| Q | 0.5 | 1 | 1 | 1 | 2 | 5 | 1 | 1 | 2 | 1 | 1 | 1 | — | 1 | 1 | — | 1 | 1 | — | 1 | 1 |
| | 1 | 1.5 | 2 | 2.5 | 2.5 | 2.5 | 2.5 | 2 | 4 | 3.5 | 2 | 2.5 | 1 | 2.5 | 2.5 | 1 | 1.5 | 2.5 | 5 | 1.5 | 3.5 |
| | 2 | 2.5 | 3 | 3 | 3 | 5 | 4 | 2.5 | 5 | 4 | 2 | 3 | 2 | 3 | 3 | 2 | 3.5 | 4 | 2 | 3.5 | 3.5 |
| | 4 | 5 | 5 | 5 | 5 | 5 | 5 | 4 | 5 | 5 | 5 | 4 | 4 | 4 | 5 | 5 | 4 | 5 | 4 | 4 | 5 |
| R | 0.2 | 1 | 1 | 1 | 1 | 4 | 3 | 2 | 4 | 4 | 2 | 2 | 1 | 3 | 5 | 4 | 3 | 2 | — | 2 | 4 |
| | 0.5 | 2 | 3 | 2 | 2 | 4 | 3 | 2 | 5 | 4 | 3 | 4 | 3 | 4 | 5 | 4 | 4 | 3 | — | 4 | 5 |
| | 1 | 2 | 4 | 4 | 3 | 5 | 5 | 5 | 5 | 5 | 5 | 3 | 4 | 5 | 5 | 5 | 4 | 4 | 4 | 4 | 5 |
| | 2 | 3 | 4.5 | 4.5 | 4 | 5 | 4 | 3 | 5 | 4.5 | 4.5 | 4.5 | 4 | 4.5 | 5 | 5 | 5 | 4.5 | 5 | 4.5 | 5 |
| | 4 | 5 | 5 | 5 | 5 | 5 | 5 | 4 | 5 | 5 | 5 | 3 | 5 | 5 | 5 | 5 | 5 | 5 | 5 | 5 | 5 |
| S | 0.2 | 1 | 1 | 1 | 1 | 1 | 1 | 1 | 1 | 1 | 1 | 1 | — | 1 | 1 | 1 | 1 | 1 | 1 | 1 | 1 |
| | 0.5 | 1 | 1 | 1 | 1 | 2 | 3 | 1 | 3 | 2.5 | 2 | 3 | — | 1.5 | 1.5 | 2.5 | 2 | 1 | 3.5 | 1 | 3.5 |
| | 1 | 1.5 | 1 | 1.5 | 1.5 | 3 | 3.5 | 2 | 3 | 2.5 | 2 | 3 | — | 4 | 2.5 | 2.5 | 2 | 2 | 4.5 | 2 | 4 |
| | 2 | 2 | — | 2 | 2 | 3 | 4 | 2 | 5 | 4 | 3 | 4 | — | 4 | 3 | 4 | 3 | 3 | 4 | 2 | 5 |
| T | 0.5 | 1 | — | 1 | 1 | 2 | 3 | 2 | 3 | 2 | 2 | 3 | — | 3 | 3 | 4 | 2 | 3 | 3 | 2 | 3 |
| | 1 | 2 | — | 2 | 2 | 3 | 4 | 2 | 4 | 3 | 2 | 4 | — | 3 | 4 | 5 | 2 | 3 | 4 | 3 | 4 |
| | 2 | 2 | — | 2 | 2 | 3 | 3 | 2 | 5 | 3 | 3 | 3 | — | 5 | 4 | 5 | 2 | 3 | 4 | 3 | 5 |
| U | 0.2 | 0.5 | 0 | 0 | 0.5 | 3 | 2 | 0 | 2 | 2 | 0.5 | 2 | 0 | 2 | 3.5 | 3 | 1 | 1 | — | 0 | 2 |
| | 0.5 | 0.3 | 1 | 0.5 | 1.3 | 3 | 3 | 0.3 | 3.3 | 3.3 | 0.6 | 2 | 0.6 | 2.3 | 3.6 | 3 | 1 | 1.3 | — | 1 | 4 |
| | 1 | 1.3 | 2.3 | 2 | 2.3 | 3.6 | 3 | 1.3 | 3.6 | 4 | 1.6 | 2.6 | 4 | 4 | 4 | 4 | 2.6 | 2.6 | — | 1.6 | 3.6 |
| | 2 | 3 | 3 | 3 | 3 | 4 | 3 | 2.5 | 4 | 4 | 3 | 4 | 4 | 4 | 4 | 4 | 3.5 | 3 | 3 | 3.5 | 4 |
| | 4 | 4 | 4 | 4 | 4 | 4 | 4 | 4 | 4 | 4 | 2 | 4 | 4 | 4 | 4 | 4 | 4 | 4 | 3 | 4 | |
| V | 1 | 0 | 0 | 1 | 1 | 1 | 1 | 1 | 1 | 1 | 2 | 2 | — | 3 | 2 | 1 | 1 | 1 | 1 | 1 | 1 |
| | 2 | 1 | 0 | 1 | 2 | 4 | 3 | 1 | 3 | 3 | 2 | 2 | 0 | 3 | 3 | 2 | 2 | 2 | 3 | 3 | 3 |
| | 4 | 1 | 1 | 2 | 2 | 4 | 3 | 1 | 3 | 3 | 2 | 4 | 0 | 3 | 4 | 4 | 3 | 3 | 3 | 3 | 2 |
| W | 0.2 | 1 | 1 | 1 | 1 | 3 | 3 | 1 | 2 | 1 | 1 | 2 | 1 | 3 | 4 | 2 | 1 | 1 | — | 1 | 2 |
| | 0.5 | 1 | 1 | 1 | 1.5 | 4 | 3.5 | 1 | 2.5 | 6 | 2 | 3 | 2 | 4 | 4.5 | 3 | 2.5 | 2 | — | 1.5 | 3 |
| | 1 | 2 | 4 | 3 | 3 | 4 | 4 | 2 | 4 | 4 | 3 | 3 | 4 | 5 | 5 | 5 | 4 | 3 | 5 | 3 | 5 |
| | 2 | 4 | 4 | 4 | 4 | 4.5 | 2.5 | 4 | 5 | 5 | 4 | 3.5 | 5 | 4.5 | 5 | 5 | 5 | 4 | 5 | 3.5 | 5 |
| | 4 | 5 | 5 | 5 | 5 | 5 | 4 | 5 | 5 | 5 | 5 | 3 | 5 | 5 | 5 | 5 | 5 | 5 | 5 | 5 | 5 |
| X | 0.2 | 1 | 1.5 | 1 | 1 | 3 | 4 | 1.5 | 2.5 | 3 | 2.5 | 3.5 | 1 | 3 | 4 | 4 | 2.5 | 2 | — | 1 | 3 |
| | 0.5 | 2 | 2 | 1 | 2 | 3 | 4 | 1 | 5 | 5 | 3 | 4 | 2 | 4 | 5 | 4 | 4 | 3 | — | 2 | 5 |
| | 1 | 3 | 4 | 3 | 3 | 5 | 5 | 3 | 5 | 5 | 4 | 4 | 3 | 5 | 5 | 5 | 5 | 4 | — | 3 | 4 |
| | 2 | 4 | 4.5 | 4 | 4 | 5 | 4.5 | 3 | 5 | 5 | 4.5 | 4.5 | 5 | 5 | 5 | 5 | 5 | 4.5 | 5 | 4 | 5 |
| | 4 | 5 | 5 | 5 | 5 | 5 | 5 | 5 | 5 | 5 | 5 | 4 | 5 | 5 | 5 | 6 | 5 | 5 | 5 | 4 | 5 |
| Y | 0.2 | 1 | 1 | 1 | 1 | 1 | 2 | 1 | 2 | 1 | 1 | 4 | 1 | 1 | 1 | 1 | 1 | 1 | — | 1 | 2 |
| | 0.5 | 1 | 1 | 1 | 1 | 1 | 1.5 | 1 | 2 | 1.5 | 1.5 | 4 | 1 | 2 | 4 | 2.5 | 2 | 1.5 | — | 2 | 1.5 |
| | 1 | 1 | 3 | 2 | 3 | 3 | 4 | 2 | 4 | 3 | 2 | 4 | 2 | 4 | 4 | 4 | 3 | 3 | 5 | 2 | 3 |
| | 2 | 2 | 3.5 | 3.5 | 4 | 5 | 5 | 3 | 4.5 | 5 | 3.5 | 5 | 3.5 | 4.5 | 5 | 5 | 4 | 4.5 | 5 | 3.5 | 4 |
| | 4 | 4 | 5 | 5 | 5 | 5 | 5 | 5 | 5 | 5 | 4 | 5 | 5 | 5 | 5 | 5 | 5 | 5 | 4 | 5 | 5 |
| Z | 0.2 | 1 | 1 | 1 | 1 | 1 | 4 | 1 | 1 | 1 | 1.5 | 4 | 1.5 | 1.5 | 1.5 | 1.5 | 1.5 | 1 | — | 1 | 1.6 |
| | 0.5 | 1 | 1 | 1 | 1 | 3 | 4 | 2 | 2 | 2 | 3 | 4 | 1 | 3 | 3 | 3 | 2 | 2 | — | 3 | 3 |
| | 1 | 1 | 1 | 3 | 3 | 4 | 5 | 3 | 4 | 4 | 4 | 4 | 2 | 5 | 5 | 5 | 4 | 4 | 4 | 3 | 5 |
| | 2 | 3 | 3 | 3 | 3 | 4 | 5 | 3 | 5 | 5 | 4.5 | 4.5 | 5 | 5 | 5 | 5 | 5 | 5 | 4 | 3.5 | 5 |
| | 4 | 3.5 | 3.5 | 3 | 4 | 5 | 5 | 4 | 5 | 5 | 5 | 5 | 5 | 5 | 5 | 5 | 5 | 5 | 5 | 5 | 5 |
| AA | 0.2 | 1 | 1 | 1 | 1 | 1 | 1 | 1 | 3 | 1 | 2 | 2 | 1 | 1 | 2 | 1 | 1 | 1 | — | 1 | 2 |
| | 0.5 | 1 | 1 | 1 | 1 | 2.5 | 4.5 | 1 | 2.5 | 2 | 2 | 4 | 2 | 2.5 | 4 | 3 | 2 | 2 | — | 2 | 3.5 |
| | 1 | 2 | 3 | 2 | 3 | 4 | 5 | 2 | 4 | 5 | 3 | 3 | 2.5 | 4 | 5 | 5 | 3 | 3 | 4 | 3 | 5 |
| | 2 | 2.5 | 3.5 | 3.5 | 4 | 4.5 | 5 | 3 | 4.5 | 4.5 | 4 | 4 | 3 | 4.5 | 5 | 5 | 4.5 | 4 | 5 | 3.5 | 5 |
| | 4 | 5 | 5 | 5 | 5 | 5 | 5 | 4 | 5 | 5 | 5 | 5 | 5 | 5 | 5 | 5 | 5 | 5 | 5 | 5 | 5 |
| AB | 0.5 | 1 | 1 | 1 | 1 | 1 | 4 | 1 | 3 | 2 | 3 | 2 | 2 | 2 | 3 | 3 | 2 | 3 | 3 | 3 | 2 |
| | 1 | 1 | 2.5 | 1.5 | 1.5 | 2 | 3 | 1 | 3 | 3 | 1.5 | 3 | 1 | 2.5 | 4 | 2 | 3 | 3.5 | 3.5 | 3 | 3.5 |
| | 2 | 2.5 | 5 | 4 | 2.5 | 4.5 | 4 | 2.5 | 4.5 | 3.5 | 2 | 2.5 | 1 | 3.5 | 4.5 | 3 | 3.5 | 3.5 | 4.5 | 3.5 | 4.5 |
| | 4 | 3 | 3 | 3 | 3 | 5 | 4 | 2 | 5 | 4 | 4 | 1 | 4 | 4 | 4 | 5 | 4 | 4 | 3 | 4 | |
| AC | 0.2 | 1 | 1 | 1 | 1 | 1 | 1 | 1 | 1 | 1 | 1 | 1 | — | 1 | 1 | 1 | 1 | 1 | 1 | 1 | 1 |

CHART 1-continued

| Cpd. | Appln. Rate Lb./A. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
|  | 0.5 | 1 | 1 | 1 | 1 | 1 | 1 | 1 | 1 | 1 | 3 | 3 | — | 2 | 1 | 3 | 2 | 1 | 3 | 1 | 1 |
|  | 1 | 1 | 1 | 1 | 1 | 2 | 2 | 1.5 | 2 | 2 | 2 | 3 | — | 3 | 4 | 3 | 2.5 | 2 | 3.5 | 1.5 | 2.5 |
|  | 2 | 2 | 2 | 2 | 3 | 4 | 4 | 3 | 4 | 3 | 3 | 4 | — | 4 | 4 | 4 | 3 | 3 | 4 | 3 | 4 |
|  | 4 | 1 | 1 | 2 | 2 | 3 | 4 | 2 | 4 | 2 | 2 | 4 | — | 4 | 3 | 3 | 3 | 4 | 2 | 4 |
| AD | 0.2 | 1 | 1 | 1 | 1 | 1 | 2 | 1 | 2 | 1 | 1 | 3 | — | 1 | 1 | 3 | 1 | 1 | 2 | 1 | 1 |
|  | 0.5 | 1 | 1 | 1 | 1.5 | 2.5 | 3 | 1 | 3.5 | 2.5 | 1.5 | 2.5 | — | 3 | 3 | 3 | 2 | 1 | 2.5 | 1.5 | 2.5 |
|  | 1 | 1 | 1 | 1 | 2 | 2 | 4 | 1 | 3 | 2 | 3 | 3 | — | 3 | 4 | 2 | 2 | 3 | 3 | 4 |
|  | 2 | 1.5 | 1.5 | 2.5 | 2.5 | 4 | 4 | 1.5 | 4.5 | 4 | 3.5 | 4 | — | 4.5 | 4 | 4 | 3 | 3 | 4 | 4.5 | 5 |
|  | 4 | 2 | 1 | 3 | 2 | 4 | 4 | 2 | 5 | 4 | 4 | 4 | — | 4 | 4 | 4 | 3 | 4 | 3 | 5 |
| AE | 0.2 | 1 | 1 | 1 | 1 | 1 | 2 | 1 | 2 | 2 | 2 | 3 | 1 | 4 | 3 | 1 | 1 | 2 | 1 | 1 |
|  | 0.5 | 1 | 1 | 1 | 2 | 1 | 3 | 1 | 2 | 1 | 2 | 4 | 1 | 3 | 4 | 3 | 1 | 2 | 3 | 2 | 2 |
|  | 1 | 1 | 1 | 1 | 2 | 2 | 3 | 1 | 4 | 2 | 3 | 4 | 1 | 4 | 2 | 3 | 2 | 2 | 3 | 2 | 3 |
|  | 2 | 3 | 2 | 4 | 3 | — | 5 | 2 | 5 | 5 | 4 | — | — | 5 | 4 | — | 4 | 4 | 4 | 4 | 5 |
| AF | 0.2 | 1 | 1 | 1 | 1 | 1 | 1 | 1 | 1 | 1 | 1 | 1 | — | 1 | 1 | 1 | 1 | 1 | 1 | 1 |
|  | 0.5 | 1 | 1 | 1 | 1 | 1 | 1 | 1 | 1 | 1 | 3 | 2 | — | 2 | 1 | 2 | 2 | 1 | 1 | 1 | 1 |
|  | 1 | 1 | 1 | 1 | 1 | 1.5 | 2.5 | 2 | 2 | 1.5 | 3 | 3.5 | — | 3 | 2.5 | 3.5 | 2.5 | 1.5 | 3.5 | 1.5 | 2 |
|  | 2 | 1 | 1 | 1 | 2 | 2 | 3 | 2 | 4 | 3 | 2 | 4 | — | 3 | 3 | 4 | 3 | 2 | 5 | 2 | 3 |
|  | 4 | 2 | 1 | 2 | 2 | 3 | 3 | 2 | 5 | 4 | 3 | 4 | — | 3 | 3 | 4 | 4 | 3 | 5 | 3 | 5 |
| AG | 0.2 | 1 | 1 | 1 | 1 | 1 | 2 | 1 | 1 | 1 | — | 2 | — | 2 | 1 | 2 | 2 | 1 | 2 | 1 | 2 |
|  | 0.5 | 1 | 1 | 1 | 1 | 1 | 2 | 1 | 1 | 1 | — | 3 | — | 3 | 1 | 3 | 2 | 2 | 3 | 2 | 2 |
|  | 1 | 1 | 1 | 1 | 2 | 2 | 3 | 1 | 2 | 1 | 3 | 3 | — | 4 | 3 | 3 | 2 | 1 | 4 | 1 | 4 |
|  | 2 | 2 | 2 | 1 | 2 | 2 | 3 | 2 | 3 | 3 | 3 | 4 | — | 4 | 3 | 4 | 3 | 2 | 4 | 2 | 4 |
|  | 4 | 2 | 2 | 3 | 3 | 3 | 3 | 2 | 5 | 4 | 4 | 4 | — | 4 | 4 | 4 | 3 | 2 | 4 | 2 | 5 |
| AH | 0.5 | 1 | 1 | 1 | 1 | 2 | 1 | 1 | 1 | 1 | 2 | 2 | 1 | 3 | 4 | — | 3 | 1 | — | 2 | 1 |
|  | 1 | 3 | 3 | 3 | 3.5 | 5 | 4 | 3 | 4 | 4 | 2.5 | 3.5 | 5 | 4.5 | 5 | 5 | 3 | 4.5 | 5 | 4 | 4 |
|  | 2 | 3.5 | 3 | 3 | 3.5 | 5 | 4 | 3 | 4.5 | 5 | 3.5 | 3 | 5 | 4.5 | 4.5 | 5 | 4.5 | 4 | 5 | 4 | 5 |
|  | 4 | 5 | 5 | 5 | 5 | 5 | 5 | 4 | 5 | 5 | 5 | 3 | 5 | 5 | 5 | 5 | 5 | 5 | 5 | 5 | 5 |
| AI | 0.2 | 1 | 1 | 1 | 1 | 1 | 1 | 1 | 1 | 1 | 1 | 1 | 1 | 1 | 1 | 1 | 1 | 1 | 1 | 1 | 1 |
|  | 0.5 | 1.5 | 1 | 1 | 1 | 3 | 3 | 1 | 1.5 | 2 | 1.5 | 2 | 1 | 1.5 | 3 | 3 | 2 | 1 | 2.5 | 1.5 | 1 |
|  | 1 | 2 | 1 | 1 | 2 | 3 | 4 | 1 | 3 | 3 | 3 | 3 | 2 | 4 | 4 | 4 | 3 | 2 | 2 | 3 | 4 |
|  | 2 | 3 | 3 | 3 | 3 | 5 | 4 | 2 | 5 | 5 | 4 | 4 | 2 | 4 | 5 | 4 | 5 | 4 | — | 5 | 5 |
|  | 4 | 3 | 5 | 4 | 3 | 4 | 4 | 2 | 5 | 5 | 5 | 3 | 5 | 5 | 5 | 5 | 4 | 4 | — | 5 | 5 |
| AJ | 0.5 | 1 | 1 | 1 | 1 | 1 | 1 | 1 | 1 | 1 | 2 | 3 | 2 | 1 | 3 | 2 | 1 | 2 | 2 | 1 | 1 |
|  | 1 | 1 | 1 | 1 | 1 | 1 | 2 | 1.5 | 2.5 | 2.5 | 2 | 4 | 2 | 2.5 | 3.5 | 4 | 2.5 | 3 | 4 | 3 | 4 |
|  | 2 | 1.5 | 1 | 1 | 1.5 | 2.5 | 4 | 1.5 | 3.5 | 4.5 | 3 | 4 | 2 | 4 | 4.5 | 3.5 | 4 | 2.5 | 4 | 4.5 | 5 |
|  | 4 | 2 | 3 | 3 | 2 | 5 | 4 | 1 | 4 | 5 | 3 | 5 | 5 | 4 | 5 | 4 | 4 | — | 5 | 5 |

For the postemergence testing, seven plant species were used. These were planted in rows perpendicular to the long axis of the flat, one species per row. The seven plant species used, numbered consecutively for identification purposes in Chart 2, and the approximate number of seeds planted were as follows:

1. Corn (*Zea mays*) 4
2. Large Crabgrass (*Digitaria sanguinalis*) 350
3. Pigweed (*Amaranthus retroflexus*) 350
4. Foxtail Millet (*Setaria italica*) 200
5. Velvetleaf (*Abutilon theophrasti*) 100
6. Morning Glory (*Ipomoea purpurea*) 25
7. Zinnia (*Zinnia elegans*) 20

After planting, the seeds were covered with 0.5 to 1.0 cm. of screened sterilized (24 hours) soil. Two and one-half grams of soluble fertilizer (23–19–17) were applied to each flat during the initial watering. The postemergence flats were planted 10–13 days prior to treatment and were placed in a growth chamber until the day of treatment. In the growth room, flats received 12 to 18 hours of light a day, depending on light intensity, and were subjected to a temperature of about 74°–80° F.

The formulation of the test compounds was accomplished in the same manner as described above for the test compounds used in the preemergence testing. The chemicals were applied with a modified De Vilbiss atomizer using an air pressure of 10–12 psi. Each flat received 12.5 ml. of solution. After treatment, all flats were transferred to greenhouses for 12–13 days. Herbicidal effects were then rated on each plant species. The ratings are the same as those used in the preemergence test above.

The results of the above trials are set forth in Chart 2 which follows. In the Chart, column 1 gives the identification of the compound under test; column 2, the rate in lbs./A. at which the compound was applied to the test flat; and the remaining columns, the injury rating for the particular plant seeds or seedlings, the species being identified by number.

CHART 2

| Cpd. | Appln. Rate Lb./A. | 1 | 2 | 3 | 4 | 5 | 6 | 7 |
|---|---|---|---|---|---|---|---|---|
| A | 0.2 | 2 | 3 | 4 | 5 | 4 | 4 | 5 |
|  | 0.5 | 4 | 4 | 5 | 5 | 5 | 5 | 5 |
|  | 1 | 4 | 5 | 5 | 5 | 5 | 5 | 5 |
|  | 2 | 5 | 5 | 5 | 5 | 5 | 5 | 5 |
|  | 4 | 5 | 5 | 5 | 5 | — | 5 | 5 |
| B | 0.2 | 1 | 2 | 3 | 3 | — | 2 | 5 |
|  | 0.5 | 2 | 3 | 3.5 | 5 | — | 3 | 5 |
|  | 1 | 2 | 3 | 4 | 4 | 5 | 3 | 5 |
|  | 2 | 2.5 | 4.5 | 5 | 5 | 5 | 4 | 5 |
|  | 4 | 4 | 5 | 5 | 5 | 5 | 5 | 5 |
| C | 0.2 | 1 | 3 | 3 | 4 | 1 | 2 | 3 |
|  | 0.5 | 1 | 4 | 3 | 4 | 3 | 3 | 5 |
|  | 1 | 2 | 5 | 4 | 5 | 4 | 3 | 5 |
|  | 2 | 3.5 | 5 | 4.5 | 5 | 4 | 3 | 4.5 |
| D | 0.2 | 2 | 3 | 4 | 4 | 3 | 4 | 5 |
|  | 0.5 | 2 | 3 | 3 | 5 | 4 | 4 | 5 |
|  | 1 | 2 | 4 | 5 | 5 | 4 | 5 | 5 |
|  | 2 | 4 | 5 | 5 | 5 | 4.5 | 5 | 5 |
|  | 4 | 3 | 4 | 5 | 5 | 3 | 5 | 4 |
| E | 0.2 | 2 | 3 | 3 | 3 | 3 | 4 | 4 |
|  | 0.5 | 2 | 4 | 4 | 5 | 4 | 5 | 4 |
|  | 1 | 2.5 | 4.5 | 4.5 | 4.5 | 4.5 | 4.5 | 5 |
|  | 2 | 4 | 5 | 5 | 5 | 5 | 5 | 5 |
| F | 0.2 | 0.5 | 2.5 | 3.5 | 2 | — | 1.5 | 4 |
|  | 0.5 | 1 | 3.3 | 3.5 | 3.3 | — | 2.3 | 4 |
|  | 1 | 2.3 | 3 | 4 | 4 | — | 3 | 4 |
|  | 2 | 4 | 4 | 4 | 4 | 4 | 3 | 4 |
|  | 4 | 4 | 4 | 4 | 4 | 4 | 4 | 4 |
| G | 0.2 | 0.6 | 2.6 | 3.3 | 2.6 | — | 1.6 | 4 |
|  | 0.5 | 1.5 | 3.5 | 3.5 | 3 | — | 2 | 4 |
|  | 1 | 2.5 | 3.5 | 4 | 3.5 | 4 | 2.5 | 4 |
|  | 2 | 4 | 4 | 4 | 4 | 4 | 3 | 4 |
|  | 4 | 4 | 4 | 4 | 4 | 4 | 4 | 4 |
| H | 0.2 | 1 | 3 | 4 | 3 | 3 | 3 | 3 |
|  | 0.5 | 1.5 | 3 | 4 | 4 | 3.5 | 4 | 4 |
|  | 1 | 2.5 | 4 | 4.5 | 4 | 4 | 4.5 | 5 |
|  | 2 | 3.5 | 5 | 5 | 4.5 | 5 | 5 | 5 |

CHART 2-continued

| Cpd. | Appln. Rate Lb./A. | 1 | 2 | 3 | 4 | 5 | 6 | 7 |
|---|---|---|---|---|---|---|---|---|
| I | 0.2 | 2 | 5 | 5 | 5 | 2 | 2 | 5 |
|  | 0.5 | 2 | 5 | 5 | 5 | 2 | 2 | 4 |
|  | 1 | 2 | 5 | 5 | 5 | 4 | 3 | 4 |
|  | 2 | 3.5 | 5 | 4.5 | 5 | 3 | 2.5 | 5 |
|  | 4 | 4 | 5 | 5 | 5 | 3 | 3 | 5 |
| J | 0.2 | 0 | 4 | 4 | 4 | 3.5 | 4 | 4 |
|  | 0.5 | 2 | 3 | 4 | 4 | 4 | 4 | 4 |
|  | 1 | 2 | 3 | 4 | 4.5 | 4 | 3.5 | 4 |
|  | 2 | 2.5 | 3.5 | 4 | 4 | 4 | 4 | 4.5 |
| K | 0.2 | 1 | 3 | 2 | 4 | 3 | 3 | 3 |
|  | 0.5 | 2 | 3 | 3.5 | 4 | 2.5 | 3.5 | 4 |
|  | 1 | 2 | 3.5 | 4.5 | 5 | 3.5 | 4.5 | 4.5 |
|  | 2 | 3 | 4 | 4 | 4.5 | 4 | 4.5 | 5 |
| L | 0.2 | 2 | 3 | 3 | 4 | 3 | 4 | 4 |
|  | 0.5 | 1 | 3 | 3 | 4 | 3 | 4 | 4 |
|  | 1 | 2.5 | 3.5 | 4 | 4 | 3.5 | 4.5 | 4.5 |
|  | 2 | 2 | 4 | 5 | 4.5 | 4.5 | 4.5 | 5 |
| M | 0.2 | 1 | 2.5 | 4 | 3.5 | 2 | 4.5 | 4 |
|  | 0.5 | 1 | 3 | 3 | 4 | 3 | 4 | 4 |
|  | 1 | 1 | 3 | 4 | 4 | 3 | 4.5 | 4.5 |
|  | 2 | 2 | 3 | 4 | 4.5 | 3 | 1.5 | 4.5 |
| N | 0.2 | 1 | 2 | 2 | 2 | — | 1 | 3 |
|  | 0.5 | 2 | 3.5 | 3 | 3 | — | 1.5 | 5 |
|  | 1 | 3 | 4 | 5 | 4 | 5 | 3 | 5 |
|  | 2 | 4.5 | 5 | 5 | 5 | 5 | 3.5 | 5 |
|  | 4 | 5 | 5 | 5 | 5 | 5 | 4 | 5 |
| O | 0.2 | 2 | 4 | 4 | 5 | 4 | 4 | 5 |
|  | 0.5 | 3 | 5 | 5 | 5 | 4 | 4 | 5 |
|  | 1 | 4 | 5 | 5 | 5 | 5 | 4 | 5 |
|  | 2 | 5 | 5 | 5 | 5 | 4.5 | 4 | 5 |
|  | 4 | 5 | 5 | 5 | 5 | 5 | 5 | 5 |
| P | 0.2 | 1 | 3 | 3 | 4 | 3 | 2 | 4 |
|  | 0.5 | 1 | 4 | 4 | 5 | 4 | 3 | 5 |
|  | 1 | 2 | 4 | 4 | 5 | 5 | 4 | 5 |
|  | 2 | 4 | 5 | 4.5 | 5 | 5 | 3.5 | 5 |
|  | 4 | 5 | 5 | 5 | 5 | 5 | 4 | 5 |
| Q | 0.5 | 1 | 2 | 2 | 2 | — | 1 | 3 |
|  | 1 | 1 | 3 | 2.5 | 3 | 5 | 2.5 | 4 |
|  | 2 | 3 | 4.5 | 4 | 4 | 5 | 3.5 | 5 |
|  | 4 | 4 | 5 | 5 | 5 | 5 | 4 | 5 |
| R | 0.2 | 1 | 2 | 4.5 | 4 | — | 2.5 | 4 |
|  | 0.5 | 2 | 3 | 4.5 | 4 | — | 3 | 5 |
|  | 1 | 3 | 4 | 5 | 4 | 5 | 4 | 5 |
|  | 2 | 3 | 4.5 | 5 | 5 | 5 | 4 | 5 |
|  | 4 | 5 | 5 | 5 | 5 | 5 | 5 | 5 |
| S | 0.2 | 1.5 | 3.5 | 5 | 4 | 4.5 | 4 | 4.5 |
|  | 0.5 | 3 | 5 | 5 | 5 | 5 | 4 | 5 |
|  | 1 | 5 | 5 | 5 | 5 | 5 | 4 | 5 |
|  | 2 | 4 | 5 | 5 | 5 | 5 | 4 | 5 |
| T | 0.2 | 1.5 | 4 | 4.5 | 4.5 | 5 | 3 | 4 |
|  | 0.5 | 2.5 | 4 | 5 | 5 | 4.5 | 3 | 4.5 |
|  | 1 | 4.5 | 4.5 | 5 | 5 | 5 | 4 | 5 |
|  | 2 | 5 | 5 | 5 | 5 | 5 | 5 | 5 |
| U | 0.2 | 0.5 | 1.5 | 2.5 | 1.5 | — | 1 | 3 |
|  | 0.5 | 0.6 | 2.6 | 3.3 | 2 | — | 1.3 | 3.3 |
|  | 1 | 1 | 2.6 | 3.6 | 3.3 | 4 | 1.6 | 3.3 |
|  | 2 | 2 | 4 | 4 | 4 | 4 | 3 | 4 |
|  | 4 | 4 | 4 | 4 | 4 | 4 | 3 | 4 |
| V | 0.2 | 1 | 3 | 3 | 4 | 2 | 3 | — |
|  | 0.5 | 2.5 | 3.5 | 4 | 4 | 3.5 | 3.5 | 4.5 |
|  | 1 | 2 | 4 | 3.5 | 4 | 4 | 4 | 4.5 |
|  | 2 | 2 | 3 | 3.5 | 4 | 4 | 4 | 4.5 |
|  | 4 | 2 | 4 | 5 | 4 | 5 | 4 | 4 |
| W | 0.2 | 2 | 3.5 | 4.5 | 3.5 | — | 3 | 4.5 |
|  | 0.5 | 2 | 4 | 4 | 4 | — | 3 | 5 |
|  | 1 | 3 | 5 | 5 | 5 | 5 | 3 | 5 |
|  | 2 | 4.5 | 5 | 5 | 5 | 5 | 3.5 | 5 |
|  | 4 | 5 | 5 | 5 | 5 | 5 | 4 | 5 |
| X | 0.2 | 1.5 | 3 | 3.5 | 3.5 | — | 2 | 5 |
|  | 0.5 | 2 | 4 | 5 | 4 | — | 3 | 5 |
|  | 1 | 4 | 5 | 5 | 5 | 5 | 4 | 5 |
|  | 2 | 5 | 5 | 5 | 5 | 5 | 5 | 5 |
|  | 4 | 5 | 5 | 5 | 5 | 5 | 4 | 5 |
| Y | 0.5 | 1 | 2 | — | 3 | — | 1 | 2 |
|  | 1 | 1 | 3 | 4.5 | 3 | 5 | 3 | 4 |
|  | 2 | 2 | 3.5 | 5 | 4.5 | — | 3.5 | 5 |
|  | 4 | 3 | 5 | 5 | 5 | — | 4 | 5 |
| Z | 0.2 | 1 | 2 | 4 | 5 | — | 2 | 5 |
|  | 0.5 | 3 | 4 | 4 | 5 | — | 3 | 5 |
|  | 1 | 2 | 4.5 | 5 | 4.5 | 5 | 3.5 | 5 |
|  | 2 | 4 | 5 | 5 | 5 | 5 | 4 | 5 |
|  | 4 | 5 | 5 | 5 | 5 | 5 | 4 | 5 |
| AA | 0.5 | 1 | 2 | — | 3 | — | 3 | 2 |
|  | 1 | 2 | 4.5 | 5 | 4.5 | 4 | 3.5 | 4.5 |
|  | 2 | 2.5 | 3.5 | 5 | 4.5 | 5 | 4 | 4.5 |
|  | 4 | 4 | 5 | 5 | 5 | 5 | 5 | 5 |
| AB | 0.5 | 2 | 2 | 3 | 2 | 3 | 2 | 3 |
|  | 1 | 1.5 | 2.5 | 4.5 | 3 | 4 | 3.5 | 3 |
|  | 2 | 2 | 2.5 | 4 | 4 | 4 | 4 | 3.5 |
|  | 4 | 2 | 4 | 5 | 4 | 5 | 4 | 5 |
| AC | 0.2 | 2.5 | 4.5 | 5 | 3.5 | 5 | 3.5 | 3.5 |
|  | 0.5 | 2 | 3 | 4 | 4 | 5 | 4 | 4 |
|  | 1 | 3.5 | 4 | 5 | 4.5 | 5 | 4.5 | 5 |
|  | 2 | 4 | 5 | 5 | 5 | 5 | 5 | 5 |
|  | 4 | 5 | 5 | 5 | 5 | 5 | 5 | 5 |
| AD | 0.2 | 1.5 | 3.5 | 4.5 | 3.5 | 4 | 2.5 | 3 |
|  | 0.5 | 2 | 4 | 4 | 4 | 4 | 3 | 4 |
|  | 1 | 4 | 5 | 5 | 5 | 5 | 4 | 5 |
|  | 2 | 4.5 | 5 | 5 | 5 | 4.5 | 4 | 5 |
|  | 4 | 5 | 5 | 5 | 5 | 5 | 5 | 5 |
| AE | 0.2 | 3 | 4 | 5 | 5 | 5 | 3 | 5 |
|  | 0.5 | 4 | 4 | 5 | 5 | 5 | 4 | 5 |
|  | 1 | 5 | 4.5 | 5 | 5 | 4.5 | 4.5 | 5 |
|  | 2 | 5 | 4.5 | 5 | 5 | 4.5 | 4.5 | 5 |
| AF | 0.2 | 2 | 4 | 5 | 4 | 5 | 2 | 3 |
|  | 0.5 | 3 | 4 | 5 | 4 | 4 | 3 | 5 |
|  | 1 | 4 | 5 | 5 | 4.5 | 5 | 4 | 5 |
|  | 2 | 4 | 5 | 5 | 5 | 5 | 5 | 5 |
|  | 4 | 5 | 5 | 5 | 5 | 5 | 5 | 5 |
| AG | 0.2 | 1.5 | 4 | 4.5 | 4 | 4.5 | 3.5 | 3.5 |
|  | 0.5 | 2 | 5 | 5 | 5 | 5 | 5 | 5 |
|  | 1 | 4 | 4.5 | 5 | 4.5 | 5 | 5 | 5 |
|  | 2 | 3 | 5 | 5 | 5 | 5 | 5 | 5 |
|  | 4 | 5 | 5 | 5 | 5 | 5 | 5 | 5 |
| AH | 0.2 | 1.5 | 2 | 3 | 3 | — | 3 | 5 |
|  | 0.5 | 2 | 4 | 3 | 4 | — | 4 | 5 |
|  | 1 | 2.5 | 5 | 5 | 5 | 5 | 5 | 5 |
|  | 2 | 4.5 | 5 | 5 | 5 | 5 | 4.5 | 5 |
|  | 4 | 5 | 5 | 5 | 5 | 5 | 5 | 5 |
| AI | 0.2 | 2 | 3 | 3 | 5 | 4 | 4 | 5 |
|  | 0.5 | 3 | 5 | 4 | 5 | 5 | 4 | 5 |
|  | 1 | 4 | 5 | 4 | 5 | 4 | 5 | 5 |
|  | 2 | 5 | 5 | 5 | 5 | 5 | 5 | 5 |
|  | 4 | 5 | 5 | 5 | 5 | 5 | 5 | 5 |
| AJ | 0.2 | 2 | 3 | 3 | 4 | 3 | 3 | 4 |
|  | 0.5 | 2.5 | 3 | 2.5 | 4 | 3.5 | 4 | 5 |
|  | 1 | 2 | 4 | 3 | 4 | 3 | 4 | 5 |
|  | 4 | 3 | 5 | 5 | 4 | — | 5 | 5 |

The herbicidal activity of other of the compounds usable in the invention was tested in accordance with the procedure hereinafter set forth. For preemergence testing, the soil in which seeds were planted was sprayed the same day with a solution containing the designated amount of product in a 50–100 percent acetone-water mixture. Observations of activity were recorded 21 to 28 days after planting and spraying. For postemergence testing, the plants were sprayed with the same solution as described above about 14 days after planting of the seeds. A vigor and kill rating was adopted to assess the phytotoxicant properties of the products. For both testing procedures, a percent kill rating for each species of plants was obtained by comparing the stand of treated plantings with untreated control plants growing under similar conditions. A vigor rating of 1 to 5 was given to those plants not killed by chemical treatment and is defined as follows:
1. severe injury, plants will die
2. moderate to severe injury, plants are not expected to recover from chemical treatment
3. moderate injury, plants are expected to show various degrees of recovery from chemical treatment
4. slight injury, plants will or have recovered and will resume normal growth
5. no apparent injury The evaluated plant species are identified below as to their corresponding Latin names:

| | |
|---|---|
| Sugar Beets: | *Beta vulgaris* |
| Corn: | *Zea mays* |
| Oats: | *Avena sativa* |
| Clover: | *Melilotus indica* |
| Soybeans: | *Glycine max* |
| Cotton: | *Gossypium hirsutum* |

-continued

| | |
|---|---|
| Mustard: | *Brassica juncea* |
| Yellow Foxtail: | *Setaria glauca* |
| Barnyard grass: | *Echinochloa crusgalli* |
| Crabgrass: | *Digitaria sanguinalis* |
| Buckwheat: | *Fagopyrum tataricum* |
| Morning Glory: | *Ipomoea purpurea* |
| Pigweed: | *Amaranthus retroflexus* |
| Jimsonweed: | *Datura stramonium* |

AL  1-[5-[N-(Methoxy)methylsulfamoyl]-1,3,4-thiadiazol-2-yl]1,3-dimethylurea

AM  1-[5-(t-Butylsulfamoyl)-1,3,4-thiadiazol-2-yl]-3-methylurea

AN  1-[5-[N-(2,2-Dimethoxyethyl)-N-methylsulfamoyl]-1,3,4-thiadiazol-2-yl]-3-methylurea AO  1-[5-[N-(2-Chloroethyl)sulfamoyl]-1,3,4-thiadiazol-2-yl]3-methylurea

Chart 3

Preemergent Activity

| Cpd. | Lbs. Per Acre | Sugar Beets Vig | Sugar Beets % Kill | Corn Vig | Corn % Kill | Oats Vig | Oats % Kill | Clover Vig | Clover % Kill | Soybeans Vig | Soybeans % Kill | Cotton Vig | Cotton % Kill | Mustard Vig | Mustard % Kill |
|---|---|---|---|---|---|---|---|---|---|---|---|---|---|---|---|
| C | 4 | | 100 | | 100 | | 100 | | 100 | | 100 | 3 | 80 | | 100 |
| | 2 | | 100 | 3 | 20 | 1 | 80 | | 100 | 3 | 0 | 4 | 20 | 3 | 60 |
| | 1 | | 100 | 4 | 0 | 1 | 80 | | 100 | 5 | 0 | 4 | 0 | 4 | 20 |
| | 0.5 | 3 | 0 | 5 | 0 | 5 | 0 | 4 | 60 | 5 | 0 | 5 | 0 | 5 | 0 |
| D | 4 | | 100 | | 100 | 1 | 80 | | 100 | | 100 | | 100 | | 100 |
| | 2 | | 100 | 1 | 60 | | 100 | | 100 | | 100 | | 100 | | 100 |
| | 1 | | 100 | 3 | 0 | 3 | 20 | | 100 | | 100 | | 100 | | 100 |
| | 0.5 | 4 | 80 | 4 | 0 | 4 | 10 | | 100 | | 100 | 4 | 0 | 3 | 60 |
| AK | 4 | | 100 | 4 | 0 | 1 | 90 | | 100 | | 100 | | 100 | | 100 |
| | 2 | | 100 | 5 | 0 | 1 | 90 | | 100 | | 100 | | 100 | | 100 |
| | 1 | | 100 | 5 | 0 | 4 | 0 | | 100 | | 100 | | 100 | | 100 |
| | 0.5 | 3 | 95 | 5 | 0 | 5 | 0 | | 100 | 3 | 40 | 4 | 0 | | 100 |

| Cpd. | Lbs. Per Acre | Yellow Foxtail Vig | Yellow Foxtail % Kill | Barnyard Grass Vig | Barnyard Grass % Kill | Crabgrass Vig | Crabgrass % Kill | Buckwheat Vig | Buckwheat % Kill | Morning Glory Vig | Morning Glory % Kill |
|---|---|---|---|---|---|---|---|---|---|---|---|
| C | 4 | | 100 | | 100 | | 100 | | 100 | 5 | 0 |
| | 2 | | 100 | | 100 | | 100 | | 100 | 5 | 0 |
| | 1 | | 100 | | 100 | | 100 | | 100 | 5 | 0 |
| | 0.5 | 4 | 0 | 3 | 40 | 4 | 20 | 4 | 0 | 5 | 0 |
| D | 4 | | 100 | | 100 | | 100 | | 100 | | 100 |
| | 2 | | 100 | | 100 | | 100 | | 100 | | 100 |
| | 1 | 3 | 80 | 2 | 90 | | 100 | | 100 | | 100 |
| | 0.5 | 3 | 0 | 3 | 30 | 3 | 40 | | 100 | | 100 |
| AK | 4 | | 100 | | 100 | | 100 | | 100 | | 100 |
| | 2 | 4 | 10 | | 100 | | 100 | | 100 | | 100 |
| | 1 | 4 | 30 | 1 | 95 | 3 | 95 | | 100 | 3 | 95 |
| | 0.5 | 4 | 0 | 2 | 90 | 4 | 0 | 3 | 60 | 3 | 90 |

Chart 4

Postemergent Activity

| Cpd. | Lbs. Per Acre | Sugar Beets Vig | Sugar Beets % Kill | Corn Vig | Corn % Kill | Oats Vig | Oats % Kill | Clover Vig | Clover % Kill | Soybeans Vig | Soybeans % Kill | Cotton Vig | Cotton % Kill | Mustard Vig | Mustard % Kill |
|---|---|---|---|---|---|---|---|---|---|---|---|---|---|---|---|
| C | 2 | | 100 | 3 | 0 | | 100 | | 100 | | 100 | | 100 | | 100 |
| | 1 | | 100 | 4 | 0 | | 100 | | 100 | 3 | 20 | 3 | 80 | | 100 |
| | 0.5 | | 100 | 5 | 0 | 3 | 60 | | 100 | 4 | 0 | 3 | 60 | | 100 |

| Cpd. | Lbs. Per Acre | Pigweed Vig | Pigweed % Kill | Jimsonweed Vig | Jimsonweed % Kill |
|---|---|---|---|---|---|
| AL | 2 | 5 | 0 | | 100 | 3 | 80 |
| AM | 2 | 5 | 0 | 3 | 50 | 3 | 0 |
| AN | 2 | 4 | 0 | | 100 | | 100 |
| AO | 2 | 5 | 0 | | 100 | 3 | 70 |

| Cpd. | Lbs. Per Acre | Yellow Foxtail Vig | Yellow Foxtail % Kill | Barnyard Grass Vig | Barnyard Grass % Kill | Crabgrass Vig | Crabgrass % Kill | Buckwheat Vig | Buckwheat % Kill | Morning Glory Vig | Morning Glory % Kill |
|---|---|---|---|---|---|---|---|---|---|---|---|
| C | 2 | | 100 | | 100 | | 100 | | 100 | 4 | 10 |
| | 1 | 3 | 95 | | 100 | | 100 | | 100 | 5 | 0 |
| | 0.5 | 3 | 80 | 1 | 90 | 3 | 30 | | 100 | 5 | 0 |
| AL | 2 | 2 | 80* | | | 2 | 90 | | | 5 | 0 |
| AM | 2 | 3 | 20* | | | 3 | 20 | | | 5 | 0 |
| AN | 2 | | 100* | | | | 100 | | | 4 | 0 |
| AO | 2 | 3 | 70* | | | 3 | 80 | | | 5 | 0 |

*Setaria italica*

The following Charts 3 and 4 show additional pre- and postemergence herbicidal activity of the compounds tested.

The test compounds not already identified above are identified by letters as set forth hereinbelow.

AK  1-Methoxy-1-methyl-3-(5-methylthio-1,3,4-thiadiazol-2-yl)urea

Field trials of the efficacy of the compounds in controlling the growth of undesirable vegetation in fallow wheatland were conducted and are illustrated by the procedures hereinafter set forth.

Experiment 1

The following procedure was used to determine the herbicidal efficacy and crop tolerance of winter wheat, Triticum sp., when a thiadiazol-2-ylurea was surface applied to fallow wheatland soon after the harvesting of the wheat grown thereon.

The compound, identified as 1-(5-t-butyl-1,3,4-thiadiazol-2-yl)-1,3-dimethylurea (Compound F, supra), formulated as an 80 percent wettable powder, was surface applied to land from which the wheat had just been harvested. This was central high tableland in Kansas. Wheat stubble remained standing in the field. The predominant weed present at the time of application was witchgrass (*Panicum capillare*). Other weeds present were Russian thistle (*Salsola kali*), Kochia or Mexican fireweed (*Kochia scoparia*), and pigweed; as well as stink grass or love grass (*Eragrostis cilianensis*), and volunteer wheat.

The experimental design was the complete randomized block. There were three replicates per treatment and each plot size was 20 by 100 feet. The previous crop grown on the site was hard Red Winter Wheat.

The herbicidal composition was applied with a hydro-pump operated from the tractor power take-off. The nozzles were located under the belly of the tractor. The herbicide was surface applied at treatment rates of 0.5 lb./acre (73.1 g./5 gal.); 1.0 lb./acre (146.2 g./5 gal.); and 2.0 lbs./acre (292.4 g./5 gal.). There was no soil incorporation of the herbicide and there was no tillage operations at the time of application.

The following spring, 234 days following the date of application of the herbicide, a weed count was made. The number of weeds per 5 sq. ft. was determined, the counts being made in five 1-foot square sections per plot. The weed present was volunteer wheat (*Triticum aestivum*).

The results are set forth in Table 1, which follows:

TABLE 1

| Treatment | Dosage lb./A. | % Weed Control |
|---|---|---|
| F (80 WP) | 0.5 | 79.2 |
|  | 1 | 96.6 |
|  | 2 | 100 |
| Control | 0 | 0 |
|  | 0 | 0 |
|  | 0 | 0 |

Eleven and one-half months after the surface application of the herbicide to the fallow land, observations of the control of unwanted vegetation on the land by the herbicide were made. The control was rated on a scale of 0 to 10, zero meaning no control, and 10 meaning 100 percent control. The results are shown in Table 2, which follows.

TABLE 2

| Treatment | lb./A. | Love-grass | Fox-tail | Witch-grass | Volunteer Wheat | Russian Thistle | Pig-weed | Kochia |
|---|---|---|---|---|---|---|---|---|
| F(80 WP) | 0.5 | 6.2 | 8.6 | 6.3 | 6.3 | 5.3 | 7 | 7 |
|  | 1 | 9.1 | 9.6 | 9.6 | 9.8 | 10 | 9.5 | 9.9 |
|  | 2 | 10 | 10 | 9.8 | 9.9 | 10 | 10 | 9.9 |
| Control | 0 | 0 | 0 | 0 | 0 | 0 | 0 | 0 |
|  | 0 | 0 | 0 | 0 | 0 | 0 | 0 | 0 |
|  | 0 | 0 | 0 | 0 | 0 | 0 | 0 | 0 |

A week after the observations recorded in Table 2, the soil was undercut with a noble blade to a depth of 4–5 inches. The soil was then tilled twice with a rod weeder before planting.

Thirteen and one-half months after the surface application of the herbicide, the land was seeded with wheat, variety Scout, at a rate of 35 lbs./A., to a depth of 3 inches, with an international drill. Two months after planting, the stand of wheat was observed to determine the extent of injury caused by the herbicide to the wheat plants. Five 2-foot sections were counted per plot, that is 10 linear feet of row were counted. The number of wheat plants in this length of the row was determined and the results are set forth in Table 3, which follows.

TABLE 3

| Treatment | lb./A. | Avg. No. of Plants Observed |
|---|---|---|
| F(80 WP) | 0.5 | 67.3 |
|  | 1 | 62.7 |
|  | 2 | 12.3 |
| Control | 0 | 82.3 |
|  | 0 | 71.3 |
|  | 0 | 65.0 |

At about 7 months, 8 months, 8.5 months, and 9 months after planting, the stands of wheat in the test plots were observed for determination of the extent of crop injury. The wheat plants were about 8 inches tall. The results are set forth in Table 4, which follows. The crop injury rating scale of 0 to 10 was used, where 0 means no injury, and 10 means the plant was killed.

TABLE 4

| Treatment | lb./A. | 7 mos. | 8 mos. | 8.5 mos. | 9 mos. |
|---|---|---|---|---|---|
| F(80 WP) | 0.5 | 0 | 0 | 0 | 0 |
|  | 1 | 1.2 | 1 | 1.6 | 1.3 |
|  | 2 | 8 | 8.1 | 7.3 | 7.7 |
| Control | 0 | 0 | 0 | 0 | 0 |
|  | 0 | 0 | 0 | 0 | 0 |
|  | 0 | 0 | 0 | 0 | 0 |

Experiment 2

The same general procedure set forth in Experiment 1 was carried out at a different location in the Central Great Plains winter wheat and range regions, again in the central high tableland, this time in Nebraska.

In this experiment, 1-(5-t-butyl-1,3,4-thiadiazol-2-yl)-1,3-dimethylurea (Compound F), formulated as an 80 percent wettable powder was surface applied to land from which the wheat had just been harvested. Wheat stubble remained standing in the field. The weeds present at the time of treatment included Russian thistle (*Salsola kali*), Kochia or Mexican fireweed (*Kochia scoparia*), pigweed, buckwheat, as well as witchgrass (*Panicum capillare*), and volunteer wheat.

The experimental design was the complete randomized block. There were three replicates per treatment and each plot size was 21 by 100 feet. The previous crop grown on the site was winter wheat, as noted.

The herbicidal composition was applied in the same manner set forth in Experiment 1. The herbicide was surface applied at treatment rates of 0.5 lb./acre; 1.0 lb./acre; and 2 lb./acre. There was no soil incorporation of the herbicide and there were no tillage operations carried on at the time of application.

One year and 5 days after the surface application of the herbicide to the fallow land, observations of the control of unwanted vegetation on the land by the herbicide were made. The control was rated on a scale of 0 to 10, zero meaning no control, and 10 meaning 100 percent control. The results are shown in the following Table 5. There were insufficient numbers of plants of Russian thistle and volunteer wheat to provide significant control ratings, so ratings for those plans are omitted.

TABLE 5

| Treatment | lb./A. | Witch-grass | Pig-weed | Kochia | Love-grass |
|---|---|---|---|---|---|
| F(80 WP) | 0.5 | 9.3 | 5.3 | 9.6 | 2.3 |
| | 1 | 8.2 | 7.6 | 9.7 | 6.3 |
| | 2 | 10.0 | 9.3 | 9.9 | 7.3 |
| Control | 0 | 0 | 0 | 0 | 0 |
| | 0 | 0 | 0 | 0 | 0 |
| | 0 | 0 | 0 | 0 | 0 |

On the same day after the above observations were made, the land was disced with a tandem disc. The land was rod weeded twice in being prepared for seeding. One month after the observations recorded in Table 5, the land was seeded with wheat, variety Trapper, at a rate of 55 lb./acre, to a depth of 3 inches below the soil surface, but covered with only 1 inch of soil. Twenty days later, the stand of wheat was observed to determine the extent of injury caused by the herbicide to the wheat plants as they developed. The number of crop plants per 10 feet of row was counted. In addition, the crop injury was observed and rated on the basis of a rating scale of 0 to 10, where 0 indicates no injury and 10 indicates death to the plants. The results of these observations are set forth in Table 6 which follows.

TABLE 6

| Treatment | lb./acre | Crop Injury | Crop Stand Count |
|---|---|---|---|
| F(80 WP) | 0.5 | 0 | 148 |
| | 1 | 0 | 157 |
| | 2 | 0.7 | 146.3 |
| Control | 0 | 0 | 152.7 |
| | 0 | 0 | 156.0 |
| | 0 | 0 | 151.7 |

The stand of wheat plants in the plots was again observed for signs of injury about 6, 7, and 8 months, respectively, after the wheat was seeded. The results are reported in Table 7, which follows, the injury rating scale being the same as that used before.

TABLE 7

| Treatment | lb./A. | 6 mos. | Crop Injury 7 mos. | 8 mos. |
|---|---|---|---|---|
| F(80 WP) | 0.5 | 0 | 0 | 0 |
| | 1 | 0 | 0 | 1 |
| | 2 | 0 | 0 | 4 |
| Control | 0 | 0 | 0 | 0 |
| | 0 | 0 | 0 | 0 |
| | 0 | 0 | 0 | 0 |

Experiment 3

The following procedure was used to determine the herbicidal efficacy and crop tolerance of winter wheat when Compound F was surface applied to fallow wheatland immediately after the 1972 harvest and prior to the planned seeding to wheat in the fall of 1973. This experiment was run in Colorado.

Compound F, formulated as an 80 percent wettable powder, was surface applied to land from which the wheat had just been harvested. Wheat stubble remained standing in the field. The following weeds were present: Kochia, pigweed, puncture vine, lambsquarter, Russian thistle and foxtail.

The herbicide was applied in the same manner as in the previous experiments. There was no soil incorporation of the herbicide.

The experimental design was the complete randomized block. There were three replicates per treatment and each plot size was 20 by 75 feet. Fifty-four days following the date of application of the herbicide, observations of the control of unwanted vegetation on the land by the herbicide were made. The control was rated on a scale of 0 to 10. The 0 meaning no control and 10 meaning 100 percent control. The results are shown in Table 8, which follows. There were insufficient numbers of plants of puncture vine, lambsquarter, and foxtail to provide significant control ratings.

TABLE 8

| Treatment | lb./A | Stink Grass | Russian thistle | Kochia | Pig-weed | Volunteer Wheat |
|---|---|---|---|---|---|---|
| F(80 WP) | 0.5 | 3.0 | 0 | 0 | 0 | 9.0 |
| | 0.75 | 5.8 | 8.2 | 9.5 | 9.0 | 10.0 |
| | 1 | 9.2 | 8.8 | 9.7 | 9.5 | 10.0 |
| | 1.5 | 9.3 | 9.2 | 10.0 | 9.7 | 10.0 |
| | 2 | 9.4 | 9.6 | 10.0 | 9.9 | 10.0 |
| Control | 0 | 0 | 0 | 0 | 0 | 0 |
| Control | 0 | 0 | 0 | 0 | 0 | 0 |

About 10 months after the date of treatment of the test plots with Compound F, observations of weed control were again made. The control ratings are the same as used before. The results are shown in Table 9, which follows.

TABLE 9

| Treatment | lb./A. | Wild Mustard | Downy Brome | Russian Thistle | Kochia | Volunteer Wheat |
|---|---|---|---|---|---|---|
| F(80 WP) | 0.5 | 7 | 9.8 | 3.6 | 4.6 | 9.8 |
| | 0.75 | 10 | 10 | 8.5 | 9.5 | 10 |
| | 1.0 | 10 | 10 | 9.7 | 9.4 | 10 |
| | 1.5 | 10 | 10 | 9.8 | 9.6 | 10 |
| | 2 | 10 | 10 | 9.8 | 9.9 | 10 |
| Control | 0 | 0 | 0 | 0 | 0 | 0 |
| | 0 | 0 | 0 | 0 | 0 | 0 |

The Russian thistle, mustard, and Kochia germinate in the spring following the fall application of the herbicide. The Russian thistle germinated in drill holes only where the stubble was very heavy. Approximately 95 percent of the volunteer wheat germinated in the fall after the date of application of Compound F.

On the same day, but after the observations set forth above in Table 9 were made, the plots were disced to a depth of 1½ inches with a tandem disc to make the soil more absorbent to moisture. The control plots were tilled to a depth of 4 inches to rid them of weeds.

Experiment 4

Another experiment similar to Experiment 3 above was run.

Compound F, formulated as an 80 percent wettable powder, was surface applied to land from which the wheat had just been harvested. This was central high tableland in Kansas. Wheat stubble remained standing in the field and the following weeds were present: Kochia, witchgrass, Russian thistle, and pigweed.

The experimental design was the complete randomized block. There were three replicates per treatment and each plot size was 20 by 75 feet.

The herbicide was applied with a power-take-off driven roller pump, the nozzles being located under the belly of the tractor. The test compound was surface applied at the rate of 0.5, 0.75, 1, 1.5, and 2 pounds per acre. There was no soil incorporation of the herbicide at the time of application.

One month following the time of application of the herbicide, observations of the control of unwanted vegetation on the land by the herbicide were made. The control was rated on the scale of 0 to 10, 0 meaning no control, and 10 meaning 100 percent control. The results are shown in the following Table 10. The buffalobur weeds germinated between the time of application of the herbicide and the observation of weed control. Since germination occurred only in the untreated plots, with only a few in the plots treated with herbicide, it was concluded that significant control had been effected.

TABLE 10

| Treatment | lb./A. | Buffalo-bur | Pig-weed | Russian Thistle | Kochia | Witch-grass |
|---|---|---|---|---|---|---|
| F(80 WP) | 0.5 | 7 | 8.3 | 1.3 | 6.3 | 4.1 |
| | 0.75 | 7.3 | 9.7 | 8.3 | 6.3 | 4.2 |
| | 1 | 8.2 | 10 | 7 | 7.7 | 6.3 |
| | 1.5 | 9.8 | 9.9 | 7.7 | 8.7 | 8.2 |
| | 2 | 9.8 | 10 | 8.6 | 10 | 9.9 |
| Control | | 0 | 0 | 0 | 0 | 0 |
| | | 0 | 0 | 0 | 0 | 0 |

Approximately 9.5 months after date of application of the herbicide, observations of the control of unwanted vegetation on the land by the herbicide were again made. The weed control was rated in the same manner as before, and the results are shown in Table 11, which follows.

TABLE 11

| Treatment | lb./A. | Russian Thistle | Kochia | Mustard | Volunteer Wheat |
|---|---|---|---|---|---|
| F(80 WP) | 0.5 | 9.9 | 10 | 10 | 10 |
| | 0.75 | 9.9 | 10 | 10 | 10 |
| | 1 | 10 | 10 | 10 | 10 |
| | 1.5 | 10 | 10 | 10 | 10 |
| | 2 | 10 | 10 | 10 | 10 |
| Control | | 0 | 0 | 0 | 0 |
| | | 0 | 0 | 0 | 0 |

Experiment 5

Another experiment similar to Experiment 4 was run.

Compound F, formulated in the same manner as described in the previous examples, was surface applied to land from which the wheat had just been harvested. This land was also central high tableland in Kansas. Wheat stubble remained standing in the field, and the following weeds, all approaching maturity, were noted as being present: Kochia, witchgrass, Russian thistle, and pigweed.

The experimental design was the complete randomized block. There were three replicates per treatment and each plot size was 20 by 75 feet.

The soil was undercut with a noble blade to a depth of about five inches. The herbicide was then applied with a power-take-off driven roller pump, the nozzles being located under the belly of the tractor. The test compound was surface applied at rates of 0.5, 0.75, 1, 1.5, and 2 pounds per acre. There was no soil incorporation of the herbicide at the time of application.

Approximately 7 and 7.5 months, respectively, following the time of application of the herbicide, observations of the control of unwanted vegetation on the land by the herbicide were made. The control was rated on the scale of 0 to 10, as described in previous examples. The results are shown in Table 12, which follows.

TABLE 12

| Treatment | lb./A. | Russian Thistle 7 | 7.5 | Kochia 7 | 7.5 | Mustard 7 | 7.5 | Volunteer Wheat 7 | 7.5 |
|---|---|---|---|---|---|---|---|---|---|
| F(80 WP) | 0.5 | 9.6 | 9.8 | 10 | 10 | 10 | 10 | 10 | 10 |
| | 0.75 | 10 | 10 | 10 | 10 | 10 | 10 | 10 | 10 |
| | 1 | 10 | 10 | 10 | 10 | 10 | 10 | 10 | 10 |
| | 1.5 | 10 | 10 | 10 | 10 | 10 | 10 | 10 | 10 |
| | 2 | 10 | 10 | 10 | 10 | 10 | 10 | 10 | 10 |
| Control | | 0 | 0 | 0 | 0 | 0 | 0 | 0 | 0 |
| | | 0 | 0 | 0 | 0 | 0 | 0 | 0 | 0 |

I claim:

1. A method for killing and preventing the growth of unwanted vegetation on fallow wheatland between the time of harvesting the wheat crop and the time of the next planting of winter wheat which method comprises applying to the locus to be treated an herbicidally-effective amount of a compound of the formula:

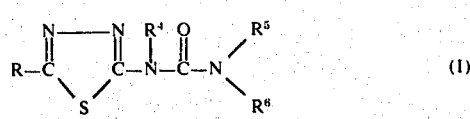

(I)

wherein
R is $C_1$-$C_7$ alkyl, or halogenated $C_1$-$C_7$ alkyl, each halogen being independently selected from the group consisting of fluorine, chlorine, and bromine,
$R^4$ is hydrogen or $C_1$-$C_7$ alkyl;
$R^5$ is hydrogen, $C_1$-$C_7$ alkyl, $C_2$-$C_7$ alkenyl, or $C_3$-$C_7$ cycloalkyl; and
$R^6$ is hydrogen, $C_2$-$C_7$ alkenyl, $C_3$-$C_7$ cycloalkyl, $C_1$-$C_4$ alkoxy, or a substituted or unsubstituted $C_1$-$C_7$ alkyl, the substituents being selected from the group consisting of halo, hydroxy, cyano, or $C_1$-$C_4$ alkoxy, except that $R^5$ and $R^6$ cannot both be hydrogen or a $C_3$-$C_7$ cycloalkyl; and, tautomers of (I) wherein $R^4$ is hydrogen; and when $R^4$ is hydrogen, the alkali metal, alkaline earth metal, and ammonium salts thereof.

2. The method of claim 1 wherein the herbicidally-effective compound is 1-(5-t-butyl-1,3,4-thiadiazol-2-yl)-1,3-dimethylurea.

3. The method of claim 2 wherein the 1-(5-t-butyl-1,3,4-thiadiazol-2-yl)-1,3dimethylurea is applied at a rate of from about 0.5 to about 2 pounds per acre.

4. The method of claim 2 wherein the 1-(5-t-butyl-1,3,4-thiadiazol-2-yl)-1,3-dimethylurea is applied at a rate of from about 0.5 to about 1.0 pound per acre.

* * * * *

UNITED STATES PATENT AND TRADEMARK OFFICE
CERTIFICATE OF CORRECTION

PATENT NO. : 3,972,706
DATED : August 3, 1976
INVENTOR(S) : Wendell Ray Arnold

It is certified that error appears in the above-identified patent and that said Letters Patent are hereby corrected as shown below:

Columns 27 and 28, in Chart 4, the % Kill of Mustard with compound C should be "100" and the Vigor should be blank.

Signed and Sealed this

Seventh Day of December 1976

[SEAL]

Attest:

RUTH C. MASON
*Attesting Officer*

C. MARSHALL DANN
*Commissioner of Patents and Trademarks*